(12) United States Patent
Ling et al.

(10) Patent No.: US 12,636,358 B2
(45) Date of Patent: May 26, 2026

(54) RECOMBINANT NON-STRUCTURAL PROTEIN 1, RECOMBINANT INFLUENZA VIRUS AND IMMUNOLOGICAL COMPOSITION INCLUDING THE SAME, AND METHOD OF TREATING OR PREVENTING DISEASE OR CONDITION CAUSED BY OR ASSOCIATED WITH INFLUENZA VIRUS

(71) Applicant: NATIONAL CHENG KUNG UNIVERSITY, Tainan City (CN)

(72) Inventors: Pin Ling, Tainan City (TW); Kuan-Ru Chen, Kaohsiung City (TW); Chun-Yang Lin, Tainan City (TW); Meng-Cen Shih, Tainan City (TW); Hung-Chuan Chang, Taichung City (TW); Kuan-Jung Lin, Tainan City (TW); Sheng-Kai Ma, Tainan City (TW)

(73) Assignee: NATIONAL CHENG KUNG UNIVERSITY, Tainan City (TW)

( * ) Notice: Subject to any disclaimer, the term of this patent is extended or adjusted under 35 U.S.C. 154(b) by 1120 days.

(21) Appl. No.: 17/616,583

(22) PCT Filed: Jun. 4, 2020

(86) PCT No.: PCT/CN2020/094471
§ 371 (c)(1),
(2) Date: Dec. 3, 2021

(87) PCT Pub. No.: WO2020/244605
PCT Pub. Date: Dec. 10, 2020

(65) Prior Publication Data
US 2022/0226463 A1    Jul. 21, 2022

Related U.S. Application Data

(60) Provisional application No. 62/856,760, filed on Jun. 4, 2019.

(51) Int. Cl.
*A61K 39/145* (2006.01)
*A61P 31/16* (2006.01)
*C07K 14/005* (2006.01)
*C12N 7/00* (2006.01)
*A61K 39/00* (2006.01)

(52) U.S. Cl.
CPC ............ *A61K 39/145* (2013.01); *A61P 31/16* (2018.01); *C07K 14/005* (2013.01); *C12N 7/00* (2013.01); *A61K 2039/5254* (2013.01); *C12N 2760/16121* (2013.01); *C12N 2760/16122* (2013.01); *C12N 2760/16134* (2013.01); *C12N 2760/16171* (2013.01)

(58) Field of Classification Search
None
See application file for complete search history.

(56) References Cited

FOREIGN PATENT DOCUMENTS

| CN | 103614345 A | 3/2014 |
|---|---|---|
| CN | 104073513 A | 10/2014 |
| CN | 107208071 A | 9/2017 |
| CN | 107964035 A | 4/2018 |
| WO | 2010101663 A2 | 9/2010 |
| WO | 2016033168 A1 | 3/2016 |

OTHER PUBLICATIONS

Qian, Wei et al., "The C-Terminal Effector Domain of Non-Structural Protein 1 of Influenza A Virus Blocks IFN-β Production by Targeting TNF Receptor-Associated Factor 3" Frontiers in Immunology, vol. 8, p. 1-16, Jul. 3, 2017.
DeDiego, Marta L. et al., "NS1 Protein Mutation I64T Affects Interferon Responses and Virulence of Circulating H3N2 Human Influenza A Viruses" Journal of Virology, vol. 90, No. 21, p. 9693-9711, Aug. 17, 2016.
Han, Han et al., "New regulatory mechanisms for the intracellular localization and trafficking of influenza A virus NS1 protein revealed by comparative analysis of A/PR/8/34 and A/Sydney/5/97" Journal of General Virology, p. 2907-2917, 2010, vol. 91.
Rodriguez, Laura et al., "Identification of Amino Acid Residues Responsible for Inhibition of Host Gene Expression by Influenza A H9N2 NS1 Targeting of CPSF30" Frontiers in Microbiology, vol. 9, p. 1-18, Oct. 24, 2018.
Hoffmann, Erich et al., "A DNA transfection system for generation of influenza A virus from eight plasmids" Proceedings of the National Academy of Sciences of the United States of America, vol. 97, No. 11, p. 6108-6113, May 23, 2000.
International Search Report of International Patent Application No. PCT/CN2020/094471 dated Sep. 7, 2020.

*Primary Examiner* — Benjamin P Blumel
(74) *Attorney, Agent, or Firm* — MCBEE MOORE & VANIK IP, LLC

(57) ABSTRACT

The present invention relates to a recombinant nonstructural protein 1 (NS 1), a recombinant influenza virus and an immunological composition including the same, as well as a method of treating or preventing a disease or condition caused by or associated with an influenza virus in a subject in need thereof. At least one amino acid residue is mutated or deleted in 4 contiguous amino acid residues of TRAF3-interacting motifs (TIMs) within an effector domain of the recombinant NS 1. A recombinant influenza virus including the recombinant NS1 is comparable to the wild-type influenza virus in virus replication ability, and the recombinant influenza virus can elevate interferon activation of a subject for achieving better immune response and better immunological protection, leading in a method of treating or preventing a disease or condition caused by or associated with an influenza virus in a subject in need thereof.

9 Claims, 14 Drawing Sheets
Specification includes a Sequence Listing.

```
                        SEQUENCE LISTING

<160> NUMBER OF SEQ ID NOS: 127

<210> SEQ ID NO 1
<211> LENGTH: 4
<212> TYPE: PRT
<213> ORGANISM: Artificial sequence
<220> FEATURE:
<223> OTHER INFORMATION: the 1st to the 4th amino acid residues of TIMs
      of wild-type NS1 of influenza A virus

<400> SEQUENCE: 1

Phe Thr Glu Glu
1

<210> SEQ ID NO 2
<211> LENGTH: 4
<212> TYPE: PRT
<213> ORGANISM: Artificial sequence
<220> FEATURE:
<223> OTHER INFORMATION: the 1st to the 4th amino acid residues of TIMs
      of the recombinant NS1

<400> SEQUENCE: 2

Phe Thr Ala Ala
1

<210> SEQ ID NO 3
<211> LENGTH: 4
<212> TYPE: PRT
<213> ORGANISM: Artificial sequence
<220> FEATURE:
<223> OTHER INFORMATION: the 1st to the 4th amino acid residues of TIMs
      of the recombinant NS1

<400> SEQUENCE: 3

Phe Ala Ala Ala
1

<210> SEQ ID NO 4
<211> LENGTH: 4
<212> TYPE: PRT
<213> ORGANISM: Artificial sequence
```

-continued

```
<220> FEATURE:
<223> OTHER INFORMATION: the 1st to the 4th amino acid residues of TIMs
      of the recombinant NS1

<400> SEQUENCE: 4

Ala Ala Ala Ala
1

<210> SEQ ID NO 5
<211> LENGTH: 4
<212> TYPE: PRT
<213> ORGANISM: Artificial sequence
<220> FEATURE:
<223> OTHER INFORMATION: the 1st to the 4th amino acid residues of TIMs
      of the recombinant NS1, Xaa refers to any amino acid except for
      Glu or none
<220> FEATURE:
<221> NAME/KEY: misc_feature
<222> LOCATION: (1)..(4)
<223> OTHER INFORMATION: Xaa can be any naturally occurring amino acid

<400> SEQUENCE: 5

Xaa Xaa Xaa Xaa
1

<210> SEQ ID NO 6
<211> LENGTH: 12
<212> TYPE: DNA
<213> ORGANISM: Artificial sequence
<220> FEATURE:
<223> OTHER INFORMATION: encoding the 1st to the 4th amino acid residues
      of TIMs of wild-type NS1 of influenza A virus

<400> SEQUENCE: 6
tttaccgaag aa                                                           12

<210> SEQ ID NO 7
<211> LENGTH: 12
<212> TYPE: DNA
<213> ORGANISM: Artificial sequence
<220> FEATURE:
<223> OTHER INFORMATION: encoding the 1st to the 4th amino acid residues
      of TIMs of the recombinant NS1

<400> SEQUENCE: 7
tttaccgcgg cg                                                           12

<210> SEQ ID NO 8
<211> LENGTH: 12
<212> TYPE: DNA
<213> ORGANISM: Artificial sequence
<220> FEATURE:
<223> OTHER INFORMATION: encoding the 1st to the 4th amino acid residues
      of TIMs of the recombinant NS1

<400> SEQUENCE: 8
tttgcggcgg cg                                                           12

<210> SEQ ID NO 9
<211> LENGTH: 12
<212> TYPE: DNA
<213> ORGANISM: Artificial sequence
<220> FEATURE:
<223> OTHER INFORMATION: encoding the 1st to the 4th amino acid residues
      of TIMs of the recombinant NS1

<400> SEQUENCE: 9
gcggcggcgg cg                                                           12
```

```
<210> SEQ ID NO 10
<211> LENGTH: 12
<212> TYPE: DNA
<213> ORGANISM: Artificial sequence
<220> FEATURE:
<223> OTHER INFORMATION: encoding the 1st to the 4th amino acid residues
      of TIMs of the recombinant NS1, v refers to not t or none, b
      refers to not a or none, d refers to not c or none, h refers to
      not g or none

<400> SEQUENCE: 10
vvvbddhbbh bb                                                              12

<210> SEQ ID NO 11
<211> LENGTH: 7
<212> TYPE: PRT
<213> ORGANISM: Artificial sequence
<220> FEATURE:
<223> OTHER INFORMATION: the -1st to the 6th amino acid residues of TIMs
      of wild-type NS1 of influenza A virus

<400> SEQUENCE: 11

Ala Phe Thr Glu Glu Gly Ala
1               5

<210> SEQ ID NO 12
<211> LENGTH: 7
<212> TYPE: PRT
<213> ORGANISM: Artificial sequence
<220> FEATURE:
<223> OTHER INFORMATION: the -1st to the 6th amino acid residues of TIMs
      of the recombinant NS1

<400> SEQUENCE: 12

Ala Phe Thr Glu Glu Gly Gly
1               5

<210> SEQ ID NO 13
<211> LENGTH: 7
<212> TYPE: PRT
<213> ORGANISM: Artificial sequence
<220> FEATURE:
<223> OTHER INFORMATION: the -1st to the 6th amino acid residues of TIMs
      of the recombinant NS1

<400> SEQUENCE: 13

Ala Phe Thr Glu Glu Ala Ala
1               5

<210> SEQ ID NO 14
<211> LENGTH: 7
<212> TYPE: PRT
<213> ORGANISM: Artificial sequence
<220> FEATURE:
<223> OTHER INFORMATION: the -1st to the 6th amino acid residues of TIMs
      of the recombinant NS1

<400> SEQUENCE: 14

Ala Phe Thr Glu Glu Ala Gly
1               5

<210> SEQ ID NO 15
<211> LENGTH: 7
<212> TYPE: PRT
<213> ORGANISM: Artificial sequence
<220> FEATURE:
<223> OTHER INFORMATION: the -1st to the 6th amino acid residues of TIMs
```

-continued of the recombinant NS1

<400> SEQUENCE: 15

Gly Phe Thr Glu Glu Gly Ala
1               5

<210> SEQ ID NO 16
<211> LENGTH: 7
<212> TYPE: PRT
<213> ORGANISM: Artificial sequence
<220> FEATURE:
<223> OTHER INFORMATION: the -1st to the 6th amino acid residues of TIMs
      of the recombinant NS1

<400> SEQUENCE: 16

Gly Phe Thr Glu Glu Gly Gly
1               5

<210> SEQ ID NO 17
<211> LENGTH: 7
<212> TYPE: PRT
<213> ORGANISM: Artificial sequence
<220> FEATURE:
<223> OTHER INFORMATION: the -1st to the 6th amino acid residues of TIMs
      of the recombinant NS1

<400> SEQUENCE: 17

Gly Phe Thr Glu Glu Ala Ala
1               5

<210> SEQ ID NO 18
<211> LENGTH: 7
<212> TYPE: PRT
<213> ORGANISM: Artificial sequence
<220> FEATURE:
<223> OTHER INFORMATION: the -1st to the 6th amino acid residues of TIMs
      of the recombinant NS1

<400> SEQUENCE: 18

Gly Phe Thr Glu Glu Ala Gly
1               5

<210> SEQ ID NO 19
<211> LENGTH: 7
<212> TYPE: PRT
<213> ORGANISM: Artificial sequence
<220> FEATURE:
<223> OTHER INFORMATION: the -1st to the 6th amino acid residues of TIMs
      of the recombinant NS1

<400> SEQUENCE: 19

Gly Ala Ala Ala Ala Ala Gly
1               5

<210> SEQ ID NO 20
<211> LENGTH: 7
<212> TYPE: PRT
<213> ORGANISM: Artificial sequence
<220> FEATURE:
<223> OTHER INFORMATION: the -1st to the 6th amino acid residues of TIMs
      of the recombinant NS1

<400> SEQUENCE: 20

Gly Phe Ala Ala Ala Ala Gly
1               5

<210> SEQ ID NO 21

```
<211> LENGTH: 7
<212> TYPE: PRT
<213> ORGANISM: Artificial sequence
<220> FEATURE:
<223> OTHER INFORMATION: the -1st to the 6th amino acid residues of TIMs
      of the recombinant NS1

<400> SEQUENCE: 21

Gly Phe Thr Ala Ala Ala Gly
1               5

<210> SEQ ID NO 22
<211> LENGTH: 7
<212> TYPE: PRT
<213> ORGANISM: Artificial sequence
<220> FEATURE:
<223> OTHER INFORMATION: the -1st to the 6th amino acid residues of TIMs
      of the recombinant NS1, Xaa refers to any amino acid except for
      Glu or none
<220> FEATURE:
<221> NAME/KEY: misc_feature
<222> LOCATION: (2)..(5)
<223> OTHER INFORMATION: Xaa can be any naturally occurring amino acid

<400> SEQUENCE: 22

Gly Xaa Xaa Xaa Xaa Ala Gly
1               5

<210> SEQ ID NO 23
<211> LENGTH: 6
<212> TYPE: PRT
<213> ORGANISM: Artificial sequence
<220> FEATURE:
<223> OTHER INFORMATION: the -1st to the 5th amino acid residues of TIMs
      of wild-type NS1 of influenza A virus

<400> SEQUENCE: 23

Ala Phe Thr Glu Glu Gly
1               5

<210> SEQ ID NO 24
<211> LENGTH: 6
<212> TYPE: PRT
<213> ORGANISM: Artificial sequence
<220> FEATURE:
<223> OTHER INFORMATION: the -1st to the 5th amino acid residues of TIMs
      of the recombinant NS1

<400> SEQUENCE: 24

Ala Phe Thr Glu Glu Ala
1               5

<210> SEQ ID NO 25
<211> LENGTH: 6
<212> TYPE: PRT
<213> ORGANISM: Artificial sequence
<220> FEATURE:
<223> OTHER INFORMATION: the -1st to the 5th amino acid residues of TIMs
      of the recombinant NS1

<400> SEQUENCE: 25

Gly Phe Thr Glu Glu Gly
1               5

<210> SEQ ID NO 26
<211> LENGTH: 6
<212> TYPE: PRT
<213> ORGANISM: Artificial sequence
<220> FEATURE:
```

-continued

```
<223> OTHER INFORMATION: the -1st to the 5th amino acid residues of TIMs
      of the recombinant NS1

<400> SEQUENCE: 26

Gly Phe Thr Glu Glu Ala
1               5

<210> SEQ ID NO 27
<211> LENGTH: 6
<212> TYPE: PRT
<213> ORGANISM: Artificial sequence
<220> FEATURE:
<223> OTHER INFORMATION: the -1st to the 5th amino acid residues of TIMs
      of the recombinant NS1

<400> SEQUENCE: 27

Gly Ala Ala Ala Ala Ala
1               5

<210> SEQ ID NO 28
<211> LENGTH: 6
<212> TYPE: PRT
<213> ORGANISM: Artificial sequence
<220> FEATURE:
<223> OTHER INFORMATION: the -1st to the 5th amino acid residues of TIMs
      of the recombinant NS1

<400> SEQUENCE: 28

Gly Phe Ala Ala Ala Ala
1               5

<210> SEQ ID NO 29
<211> LENGTH: 6
<212> TYPE: PRT
<213> ORGANISM: Artificial sequence
<220> FEATURE:
<223> OTHER INFORMATION: the -1st to the 5th amino acid residues of TIMs
      of the recombinant NS1

<400> SEQUENCE: 29

Gly Phe Thr Ala Ala Ala
1               5

<210> SEQ ID NO 30
<211> LENGTH: 6
<212> TYPE: PRT
<213> ORGANISM: Artificial sequence
<220> FEATURE:
<223> OTHER INFORMATION: the -1st to the 5th amino acid residues of TIMs
      of the recombinant NS1, Xaa refers to any amino acid except for
      Glu or none
<220> FEATURE:
<221> NAME/KEY: misc_feature
<222> LOCATION: (2)..(5)
<223> OTHER INFORMATION: Xaa can be any naturally occurring amino acid

<400> SEQUENCE: 30

Gly Xaa Xaa Xaa Xaa Ala
1               5

<210> SEQ ID NO 31
<211> LENGTH: 6
<212> TYPE: PRT
<213> ORGANISM: Artificial sequence
<220> FEATURE:
<223> OTHER INFORMATION: the 1st to the 6th amino acid residues of TIMs
      of wild-type NS1 of influenza A virus

<400> SEQUENCE: 31
```

-continued

```
Phe Thr Glu Glu Gly Ala
1               5

<210> SEQ ID NO 32
<211> LENGTH: 6
<212> TYPE: PRT
<213> ORGANISM: Artificial sequence
<220> FEATURE:
<223> OTHER INFORMATION: the 1st to the 6th amino acid residues of TIMs
      of the recombinant NS1

<400> SEQUENCE: 32

Phe Thr Glu Glu Gly Gly
1               5

<210> SEQ ID NO 33
<211> LENGTH: 6
<212> TYPE: PRT
<213> ORGANISM: Artificial sequence
<220> FEATURE:
<223> OTHER INFORMATION: the 1st to the 6th amino acid residues of TIMs
      of the recombinant NS1

<400> SEQUENCE: 33

Phe Thr Glu Glu Ala Ala
1               5

<210> SEQ ID NO 34
<211> LENGTH: 6
<212> TYPE: PRT
<213> ORGANISM: Artificial sequence
<220> FEATURE:
<223> OTHER INFORMATION: the 1st to the 6th amino acid residues of TIMs
      of the recombinant NS1

<400> SEQUENCE: 34

Phe Thr Glu Glu Ala Gly
1               5

<210> SEQ ID NO 35
<211> LENGTH: 6
<212> TYPE: PRT
<213> ORGANISM: Artificial sequence
<220> FEATURE:
<223> OTHER INFORMATION: the 1st to the 6th amino acid residues of TIMs
      of the recombinant NS1

<400> SEQUENCE: 35

Ala Ala Ala Ala Ala Gly
1               5

<210> SEQ ID NO 36
<211> LENGTH: 6
<212> TYPE: PRT
<213> ORGANISM: Artificial sequence
<220> FEATURE:
<223> OTHER INFORMATION: the 1st to the 6th amino acid residues of TIMs
      of the recombinant NS1

<400> SEQUENCE: 36

Phe Ala Ala Ala Ala Gly
1               5

<210> SEQ ID NO 37
<211> LENGTH: 6
<212> TYPE: PRT
<213> ORGANISM: Artificial sequence
```

-continued

```
<220> FEATURE:
<223> OTHER INFORMATION: the 1st to the 6th amino acid residues of TIMs
      of the recombinant NS1

<400> SEQUENCE: 37

Phe Thr Ala Ala Ala Gly
1               5

<210> SEQ ID NO 38
<211> LENGTH: 6
<212> TYPE: PRT
<213> ORGANISM: Artificial sequence
<220> FEATURE:
<223> OTHER INFORMATION: the 1st to the 6th amino acid residues of TIMs
      of the recombinant NS1, Xaa refers to any amino acid except for
      Glu or none
<220> FEATURE:
<221> NAME/KEY: misc_feature
<222> LOCATION: (1)..(4)
<223> OTHER INFORMATION: Xaa can be any naturally occurring amino acid

<400> SEQUENCE: 38

Xaa Xaa Xaa Xaa Ala Gly
1               5

<210> SEQ ID NO 39
<211> LENGTH: 5
<212> TYPE: PRT
<213> ORGANISM: Artificial sequence
<220> FEATURE:
<223> OTHER INFORMATION: the -1st to the 4th amino acid residues of TIMs
      of wild-type NS1 of influenza A virus

<400> SEQUENCE: 39

Ala Phe Thr Glu Glu
1               5

<210> SEQ ID NO 40
<211> LENGTH: 5
<212> TYPE: PRT
<213> ORGANISM: Artificial sequence
<220> FEATURE:
<223> OTHER INFORMATION: the -1st to the 4th amino acid residues of TIMs
      of the recombinant NS1

<400> SEQUENCE: 40

Gly Phe Thr Glu Glu
1               5

<210> SEQ ID NO 41
<211> LENGTH: 5
<212> TYPE: PRT
<213> ORGANISM: Artificial sequence
<220> FEATURE:
<223> OTHER INFORMATION: the -1st to the 4th amino acid residues of TIMs
      of the recombinant NS1

<400> SEQUENCE: 41

Gly Ala Ala Ala Ala
1               5

<210> SEQ ID NO 42
<211> LENGTH: 5
<212> TYPE: PRT
<213> ORGANISM: Artificial sequence
<220> FEATURE:
<223> OTHER INFORMATION: the -1st to the 4th amino acid residues of TIMs
      of the recombinant NS1
```

```
<400> SEQUENCE: 42

Gly Phe Ala Ala Ala
1               5

<210> SEQ ID NO 43
<211> LENGTH: 5
<212> TYPE: PRT
<213> ORGANISM: Artificial sequence
<220> FEATURE:
<223> OTHER INFORMATION: the -1st to the 4th amino acid residues of TIMs
      of the recombinant NS1

<400> SEQUENCE: 43

Gly Phe Thr Ala Ala
1               5

<210> SEQ ID NO 44
<211> LENGTH: 5
<212> TYPE: PRT
<213> ORGANISM: Artificial sequence
<220> FEATURE:
<223> OTHER INFORMATION: the -1st to the 4th amino acid residues of TIMs
      of the recombinant NS1, Xaa refers to any amino acid except for
      Glu or none
<220> FEATURE:
<221> NAME/KEY: misc_feature
<222> LOCATION: (2)..(5)
<223> OTHER INFORMATION: Xaa can be any naturally occurring amino acid

<400> SEQUENCE: 44

Gly Xaa Xaa Xaa Xaa
1               5

<210> SEQ ID NO 45
<211> LENGTH: 5
<212> TYPE: PRT
<213> ORGANISM: Artificial sequence
<220> FEATURE:
<223> OTHER INFORMATION: the -1st to the 5th amino acid residues of TIMs
      of wild-type NS1 of influenza A virus

<400> SEQUENCE: 45

Phe Thr Glu Glu Gly
1               5

<210> SEQ ID NO 46
<211> LENGTH: 5
<212> TYPE: PRT
<213> ORGANISM: Artificial sequence
<220> FEATURE:
<223> OTHER INFORMATION: the -1st to the 5th amino acid residues of TIMs
      of the recombinant NS1

<400> SEQUENCE: 46

Phe Thr Glu Glu Ala
1               5

<210> SEQ ID NO 47
<211> LENGTH: 5
<212> TYPE: PRT
<213> ORGANISM: Artificial sequence
<220> FEATURE:
<223> OTHER INFORMATION: the -1st to the 5th amino acid residues of TIMs
      of the recombinant NS1

<400> SEQUENCE: 47

Ala Ala Ala Ala Ala
1               5
```

```
<210> SEQ ID NO 48
<211> LENGTH: 5
<212> TYPE: PRT
<213> ORGANISM: Artificial sequence
<220> FEATURE:
<223> OTHER INFORMATION: the 1st to the 5th amino acid residues of TIMs
      of the recombinant NS1

<400> SEQUENCE: 48

Phe Ala Ala Ala Ala
1               5

<210> SEQ ID NO 49
<211> LENGTH: 5
<212> TYPE: PRT
<213> ORGANISM: Artificial sequence
<220> FEATURE:
<223> OTHER INFORMATION: the 1st to the 5th amino acid residues of TIMs
      of the recombinant NS1

<400> SEQUENCE: 49

Phe Thr Ala Ala Ala
1               5

<210> SEQ ID NO 50
<211> LENGTH: 5
<212> TYPE: PRT
<213> ORGANISM: Artificial sequence
<220> FEATURE:
<223> OTHER INFORMATION: the 1st to the 5th amino acid residues of TIMs
      of the recombinant NS1, Xaa refers to any amino acid except for
      Glu or none
<220> FEATURE:
<221> NAME/KEY: misc_feature
<222> LOCATION: (1)..(4)
<223> OTHER INFORMATION: Xaa can be any naturally occurring amino acid

<400> SEQUENCE: 50

Xaa Xaa Xaa Xaa Ala
1               5

<210> SEQ ID NO 51
<211> LENGTH: 5
<212> TYPE: PRT
<213> ORGANISM: Artificial sequence
<220> FEATURE:
<223> OTHER INFORMATION: the 2nd to the 6th amino acid residues of TIMs
      of wild-type NS1 of influenza A virus

<400> SEQUENCE: 51

Thr Glu Glu Gly Ala
1               5

<210> SEQ ID NO 52
<211> LENGTH: 5
<212> TYPE: PRT
<213> ORGANISM: Artificial sequence
<220> FEATURE:
<223> OTHER INFORMATION: the 2nd to the 6th amino acid residues of TIMs
      of the recombinant NS1

<400> SEQUENCE: 52

Thr Glu Glu Gly Gly
1               5

<210> SEQ ID NO 53
<211> LENGTH: 5
```

```
<212> TYPE: PRT
<213> ORGANISM: Artificial sequence
<220> FEATURE:
<223> OTHER INFORMATION: the 2nd to the 6th amino acid residues of TIMs
      of the recombinant NS1

<400> SEQUENCE: 53

Thr Glu Glu Ala Ala
1               5

<210> SEQ ID NO 54
<211> LENGTH: 5
<212> TYPE: PRT
<213> ORGANISM: Artificial sequence
<220> FEATURE:
<223> OTHER INFORMATION: the 2nd to the 6th amino acid residues of TIMs
      of the recombinant NS1

<400> SEQUENCE: 54

Thr Glu Glu Ala Gly
1               5

<210> SEQ ID NO 55
<211> LENGTH: 5
<212> TYPE: PRT
<213> ORGANISM: Artificial sequence
<220> FEATURE:
<223> OTHER INFORMATION: the 2nd to the 6th amino acid residues of TIMs
      of the recombinant NS1

<400> SEQUENCE: 55

Ala Ala Ala Ala Gly
1               5

<210> SEQ ID NO 56
<211> LENGTH: 5
<212> TYPE: PRT
<213> ORGANISM: Artificial sequence
<220> FEATURE:
<223> OTHER INFORMATION: the 2nd to the 6th amino acid residues of TIMs
      of the recombinant NS1

<400> SEQUENCE: 56

Thr Ala Ala Ala Gly
1               5

<210> SEQ ID NO 57
<211> LENGTH: 5
<212> TYPE: PRT
<213> ORGANISM: Artificial sequence
<220> FEATURE:
<223> OTHER INFORMATION: the 2nd to the 6th amino acid residues of TIMs
      of the recombinant NS1, Xaa refers to any amino acid except for
      Glu or none
<220> FEATURE:
<221> NAME/KEY: misc_feature
<222> LOCATION: (1)..(3)
<223> OTHER INFORMATION: Xaa can be any naturally occurring amino acid

<400> SEQUENCE: 57

Xaa Xaa Xaa Ala Gly
1               5

<210> SEQ ID NO 58
<211> LENGTH: 4
<212> TYPE: PRT
<213> ORGANISM: Artificial sequence
<220> FEATURE:
<223> OTHER INFORMATION: the 2nd to the 5th amino acid residues of TIMs
```

```
            of wild-type NS1 of influenza A virus

<400> SEQUENCE: 58

Thr Glu Glu Gly
1

<210> SEQ ID NO 59
<211> LENGTH: 4
<212> TYPE: PRT
<213> ORGANISM: Artificial sequence
<220> FEATURE:
<223> OTHER INFORMATION: the 2nd to the 5th amino acid residues of TIMs
      of the recombinant NS1

<400> SEQUENCE: 59

Thr Glu Glu Ala
1

<210> SEQ ID NO 60
<211> LENGTH: 4
<212> TYPE: PRT
<213> ORGANISM: Artificial sequence
<220> FEATURE:
<223> OTHER INFORMATION: the 2nd to the 5th amino acid residues of TIMs
      of the recombinant NS1

<400> SEQUENCE: 60

Ala Ala Ala Ala
1

<210> SEQ ID NO 61
<211> LENGTH: 4
<212> TYPE: PRT
<213> ORGANISM: Artificial sequence
<220> FEATURE:
<223> OTHER INFORMATION: the 2nd to the 5th amino acid residues of TIMs
      of the recombinant NS1

<400> SEQUENCE: 61

Thr Ala Ala Ala
1

<210> SEQ ID NO 62
<211> LENGTH: 4
<212> TYPE: PRT
<213> ORGANISM: Artificial sequence
<220> FEATURE:
<223> OTHER INFORMATION: the 2nd to the 5th amino acid residues of TIMs
      of the recombinant NS1, Xaa refers to any amino acid except for
      Glu or none
<220> FEATURE:
<221> NAME/KEY: misc_feature
<222> LOCATION: (1)..(3)
<223> OTHER INFORMATION: Xaa can be any naturally occurring amino acid

<400> SEQUENCE: 62

Xaa Xaa Xaa Ala
1

<210> SEQ ID NO 63
<211> LENGTH: 21
<212> TYPE: DNA
<213> ORGANISM: Artificial sequence
<220> FEATURE:
<223> OTHER INFORMATION: encoding the -1st to the 6th amino acid
      residues of TIMs of wild-type NS1 of influenza A virus

<400> SEQUENCE: 63
```

```
gcgtttaccg aagaaggcgc g                                              21

<210> SEQ ID NO 64
<211> LENGTH: 21
<212> TYPE: DNA
<213> ORGANISM: Artificial sequence
<220> FEATURE:
<223> OTHER INFORMATION: encoding the -1st to the 6th amino acid
      residues of TIMs of the recombinant NS1

<400> SEQUENCE: 64
gcgtttaccg aagaaggcgc g                                              21

<210> SEQ ID NO 65
<211> LENGTH: 21
<212> TYPE: DNA
<213> ORGANISM: Artificial sequence
<220> FEATURE:
<223> OTHER INFORMATION: encoding the -1st to the 6th amino acid
      residues of TIMs of the recombinant NS1

<400> SEQUENCE: 65
gcgtttaccg aagaaggcgc g                                              21

<210> SEQ ID NO 66
<211> LENGTH: 21
<212> TYPE: DNA
<213> ORGANISM: Artificial sequence
<220> FEATURE:
<223> OTHER INFORMATION: encoding the -1st to the 6th amino acid
      residues of TIMs of the recombinant NS1

<400> SEQUENCE: 66
gcgtttaccg aagaaggcgc g                                              21

<210> SEQ ID NO 67
<211> LENGTH: 21
<212> TYPE: DNA
<213> ORGANISM: Artificial sequence
<220> FEATURE:
<223> OTHER INFORMATION: encoding the -1st to the 6th amino acid
      residues of TIMs of the recombinant NS1

<400> SEQUENCE: 67
gcgtttaccg aagaaggcgc g                                              21

<210> SEQ ID NO 68
<211> LENGTH: 21
<212> TYPE: DNA
<213> ORGANISM: Artificial sequence
<220> FEATURE:
<223> OTHER INFORMATION: encoding the -1st to the 6th amino acid
      residues of TIMs of the recombinant NS1

<400> SEQUENCE: 68
gcgtttaccg aagaaggcgc g                                              21

<210> SEQ ID NO 69
<211> LENGTH: 21
<212> TYPE: DNA
<213> ORGANISM: Artificial sequence
<220> FEATURE:
<223> OTHER INFORMATION: encoding the -1st to the 6th amino acid
      residues of TIMs of wild- type NS1 of influenza A virus

<400> SEQUENCE: 69
gcgtttaccg aagaaggcgc g                                              21
```

```
<210> SEQ ID NO 70
<211> LENGTH: 21
<212> TYPE: DNA
<213> ORGANISM: Artificial sequence
<220> FEATURE:
<223> OTHER INFORMATION: encoding the -1st to the 6th amino acid
      residues of TIMs of the recombinant NS1

<400> SEQUENCE: 70
gcgtttaccg aagaaggcgc g                                           21

<210> SEQ ID NO 71
<211> LENGTH: 21
<212> TYPE: DNA
<213> ORGANISM: Artificial sequence
<220> FEATURE:
<223> OTHER INFORMATION: encoding the -1st to the 6th amino acid
      residues of TIMs of the recombinant NS1

<400> SEQUENCE: 71
gcgtttaccg aagaaggcgc g                                           21

<210> SEQ ID NO 72
<211> LENGTH: 21
<212> TYPE: DNA
<213> ORGANISM: Artificial sequence
<220> FEATURE:
<223> OTHER INFORMATION: encoding the -1st to the 6th amino acid
      residues of TIMs of the recombinant NS1

<400> SEQUENCE: 72
gcgtttaccg aagaaggcgc g                                           21

<210> SEQ ID NO 73
<211> LENGTH: 21
<212> TYPE: DNA
<213> ORGANISM: Artificial sequence
<220> FEATURE:
<223> OTHER INFORMATION: encoding the -1st to the 6th amino acid
      residues of TIMs of the recombinant NS1

<400> SEQUENCE: 73
gcgtttaccg aagaaggcgc g                                           21

<210> SEQ ID NO 74
<211> LENGTH: 21
<212> TYPE: DNA
<213> ORGANISM: Artificial sequence
<220> FEATURE:
<223> OTHER INFORMATION: encoding the -1st to the 6th amino acid
      residues of TIMs of the recombinant NS1, v refers to not t or
      none, b refers to not a or none, d refers to not c or none, h
      refers to not g or none

<400> SEQUENCE: 74
ggcvvvbddh bbhbbgcggg c                                           21

<210> SEQ ID NO 75
<211> LENGTH: 18
<212> TYPE: DNA
<213> ORGANISM: Artificial sequence
<220> FEATURE:
<223> OTHER INFORMATION: encoding the -1st to the 5th amino acid
      residues of TIMs of wild- type NS1 of influenza A virus

<400> SEQUENCE: 75
```

-continued

```
gcgtttaccg aagaaggc                                        18

<210> SEQ ID NO 76
<211> LENGTH: 18
<212> TYPE: DNA
<213> ORGANISM: Artificial sequence
<220> FEATURE:
<223> OTHER INFORMATION: encoding the -1st to the 5th amino acid
      residues of TIMs of the recombinant NS1

<400> SEQUENCE: 76
gcgtttaccg aagaagcg                                        18

<210> SEQ ID NO 77
<211> LENGTH: 18
<212> TYPE: DNA
<213> ORGANISM: Artificial sequence
<220> FEATURE:
<223> OTHER INFORMATION: encoding the -1st to the 5th amino acid
      residues of TIMs of the recombinant NS1

<400> SEQUENCE: 77
ggctttaccg aagaaggc                                        18

<210> SEQ ID NO 78
<211> LENGTH: 18
<212> TYPE: DNA
<213> ORGANISM: Artificial sequence
<220> FEATURE:
<223> OTHER INFORMATION: encoding the -1st to the 5th amino acid
      residues of TIMs of the recombinant NS1

<400> SEQUENCE: 78
ggctttaccg aagaagcg                                        18

<210> SEQ ID NO 79
<211> LENGTH: 18
<212> TYPE: DNA
<213> ORGANISM: Artificial sequence
<220> FEATURE:
<223> OTHER INFORMATION: encoding the -1st to the 5th amino acid
      residues of TIMs of the recombinant NS1

<400> SEQUENCE: 79
ggcgcggcgg cggcggcg                                        18

<210> SEQ ID NO 80
<211> LENGTH: 18
<212> TYPE: DNA
<213> ORGANISM: Artificial sequence
<220> FEATURE:
<223> OTHER INFORMATION: encoding the -1st to the 5th amino acid
      residues of TIMs of the recombinant NS1

<400> SEQUENCE: 80
ggctttgcgg cggcggcg                                        18

<210> SEQ ID NO 81
<211> LENGTH: 18
<212> TYPE: DNA
<213> ORGANISM: Artificial sequence
<220> FEATURE:
<223> OTHER INFORMATION: encoding the -1st to the 5th amino acid
      residues of TIMs of the recombinant NS1

<400> SEQUENCE: 81
gcgtttaccg aagaagcg                                        18
```

<210> SEQ ID NO 82
<211> LENGTH: 18
<212> TYPE: DNA
<213> ORGANISM: Artificial sequence
<220> FEATURE:
<223> OTHER INFORMATION: encoding the -1st to the 5th amino acid
     residues of TIMs of the recombinant NS1, v refers to not t or
     none, b refers to not a or none, d refers to not c or none, h
     refers to not g or none

<400> SEQUENCE: 82
ggcvvvbddh bbhbbgcg                                                                          18

<210> SEQ ID NO 83
<211> LENGTH: 18
<212> TYPE: DNA
<213> ORGANISM: Artificial sequence
<220> FEATURE:
<223> OTHER INFORMATION: encoding the 1st to the 6th amino acid residues
     of TIMs of wild-type NS1 of influenza A virus

<400> SEQUENCE: 83
tttaccgaag aaggcgcg                                                                          18

<210> SEQ ID NO 84
<211> LENGTH: 18
<212> TYPE: DNA
<213> ORGANISM: Artificial sequence
<220> FEATURE:
<223> OTHER INFORMATION: encoding the 1st to the 6th amino acid residues
     of TIMs of the recombinant NS1

<400> SEQUENCE: 84
tttaccgaag aaggcggc                                                                          18

<210> SEQ ID NO 85
<211> LENGTH: 18
<212> TYPE: DNA
<213> ORGANISM: Artificial sequence
<220> FEATURE:
<223> OTHER INFORMATION: encoding the 1st to the 6th amino acid residues
     of TIMs of the recombinant NS1

<400> SEQUENCE: 85
tttaccgaag aagcggcg                                                                          18

<210> SEQ ID NO 86
<211> LENGTH: 18
<212> TYPE: DNA
<213> ORGANISM: Artificial sequence
<220> FEATURE:
<223> OTHER INFORMATION: encoding the 1st to the 6th amino acid residues
     of TIMs of the recombinant NS1

<400> SEQUENCE: 86
tttaccgaag aagcgggc                                                                          18

<210> SEQ ID NO 87
<211> LENGTH: 18
<212> TYPE: DNA
<213> ORGANISM: Artificial sequence
<220> FEATURE:
<223> OTHER INFORMATION: encoding the 1st to the 6th amino acid residues
     of TIMs of the recombinant NS1

<400> SEQUENCE: 87

```
gcggcggcgg cggcgggc                                                    18

<210> SEQ ID NO 88
<211> LENGTH: 18
<212> TYPE: DNA
<213> ORGANISM: Artificial sequence
<220> FEATURE:
<223> OTHER INFORMATION: encoding the 1st to the 6th amino acid residues
      of TIMs of the recombinant NS1

<400> SEQUENCE: 88
tttgcggcgg cggcgggc                                                    18

<210> SEQ ID NO 89
<211> LENGTH: 18
<212> TYPE: DNA
<213> ORGANISM: Artificial sequence
<220> FEATURE:
<223> OTHER INFORMATION: encoding the 1st to the 6th amino acid residues
      of TIMs of the recombinant NS1

<400> SEQUENCE: 89
tttaccgcgg cggcgggc                                                    18

<210> SEQ ID NO 90
<211> LENGTH: 18
<212> TYPE: DNA
<213> ORGANISM: Artificial sequence
<220> FEATURE:
<223> OTHER INFORMATION: encoding the 1st to the 6th amino acid residues
      of TIMs of the recombinant NS1, v refers to not t or none, b
      refers to not a or none, d refers to not c or none, h refers to
      not g or none

<400> SEQUENCE: 90
vvvbddhbbh bbgcgggc                                                    18

<210> SEQ ID NO 91
<211> LENGTH: 15
<212> TYPE: DNA
<213> ORGANISM: Artificial sequence
<220> FEATURE:
<223> OTHER INFORMATION: encoding the -1st to the 4th amino acid
      residues of TIMs of wild- type NS1 of influenza A virus

<400> SEQUENCE: 91
gcgtttaccg aagaa                                                       15

<210> SEQ ID NO 92
<211> LENGTH: 15
<212> TYPE: DNA
<213> ORGANISM: Artificial sequence
<220> FEATURE:
<223> OTHER INFORMATION: encoding the -1st to the 4th amino acid
      residues of TIMs of the recombinant NS1

<400> SEQUENCE: 92
ggctttaccg aagaa                                                       15

<210> SEQ ID NO 93
<211> LENGTH: 15
<212> TYPE: DNA
<213> ORGANISM: Artificial sequence
<220> FEATURE:
<223> OTHER INFORMATION: encoding the -1st to the 4th amino acid
      residues of TIMs of the recombinant NS1

<400> SEQUENCE: 93
```
ggcgcggcgg cggcg                                                         15

<210> SEQ ID NO 94
<211> LENGTH: 15
<212> TYPE: DNA
<213> ORGANISM: Artificial sequence
<220> FEATURE:
<223> OTHER INFORMATION: encoding the -1st to the 4th amino acid
      residues of TIMs of the recombinant NS1

<400> SEQUENCE: 94
ggctttgcgg cggcg                                                         15

<210> SEQ ID NO 95
<211> LENGTH: 15
<212> TYPE: DNA
<213> ORGANISM: Artificial sequence
<220> FEATURE:
<223> OTHER INFORMATION: encoding the -1st to the 4th amino acid
      residues of TIMs of the recombinant NS1

<400> SEQUENCE: 95
ggctttaccg cggcg                                                         15

<210> SEQ ID NO 96
<211> LENGTH: 15
<212> TYPE: DNA
<213> ORGANISM: Artificial sequence
<220> FEATURE:
<223> OTHER INFORMATION: encoding the -1st to the 4th amino acid
      residues of TIMs of the recombinant NS1, v refers to not t or
      none, b refers to not a or none, d refers to not c or none, h
      refers to not g or none

<400> SEQUENCE: 96
ggcvvvbddh bbhbb                                                         15

<210> SEQ ID NO 97
<211> LENGTH: 15
<212> TYPE: DNA
<213> ORGANISM: Artificial sequence
<220> FEATURE:
<223> OTHER INFORMATION: encoding the 1st to the 5th amino acid residues
      of TIMs of wild- type NS1 of influenza A virus

<400> SEQUENCE: 97
tttaccgaag aaggc                                                         15

<210> SEQ ID NO 98
<211> LENGTH: 15
<212> TYPE: DNA
<213> ORGANISM: Artificial sequence
<220> FEATURE:
<223> OTHER INFORMATION: encoding the 1st to the 5th amino acid residues
      of TIMs of the recombinant NS1

<400> SEQUENCE: 98
tttaccgaag aagcg                                                         15

<210> SEQ ID NO 99
<211> LENGTH: 15
<212> TYPE: DNA
<213> ORGANISM: Artificial sequence
<220> FEATURE:
<223> OTHER INFORMATION: encoding the 1st to the 5th amino acid residues
      of TIMs of the recombinant NS1

-continued

```
<400> SEQUENCE: 99
gcggcggcgg cggcg                                                              15

<210> SEQ ID NO 100
<211> LENGTH: 15
<212> TYPE: DNA
<213> ORGANISM: Artificial sequence
<220> FEATURE:
<223> OTHER INFORMATION: encoding the 1st to the 5th amino acid residues
      of TIMs of the recombinant NS1

<400> SEQUENCE: 100
tttgcggcgg cggcg                                                              15

<210> SEQ ID NO 101
<211> LENGTH: 15
<212> TYPE: DNA
<213> ORGANISM: Artificial sequence
<220> FEATURE:
<223> OTHER INFORMATION: encoding the 1st to the 5th amino acid residues
      of TIMs of the recombinant NS1

<400> SEQUENCE: 101
tttaccgcgg cggcg                                                              15

<210> SEQ ID NO 102
<211> LENGTH: 15
<212> TYPE: DNA
<213> ORGANISM: Artificial sequence
<220> FEATURE:
<223> OTHER INFORMATION: encoding the 1st to the 5th amino acid residues
      of TIMs of the recombinant NS1, v refers to not t or none, b
      refers to not a or none, d refers to not c or none, h refers to
      not g or none

<400> SEQUENCE: 102
vvvbddhbbh bbgcg                                                              15

<210> SEQ ID NO 103
<211> LENGTH: 15
<212> TYPE: DNA
<213> ORGANISM: Artificial sequence
<220> FEATURE:
<223> OTHER INFORMATION: encoding the 2nd to the 6th amino acid residues
      of TIMs of wild- type NS1 of influenza A virus

<400> SEQUENCE: 103
accgaagaag gcgcg                                                              15

<210> SEQ ID NO 104
<211> LENGTH: 15
<212> TYPE: DNA
<213> ORGANISM: Artificial sequence
<220> FEATURE:
<223> OTHER INFORMATION: encoding the 2nd to the 6th amino acid residues
      of TIMs of the recombinant NS1

<400> SEQUENCE: 104
accgaagaag gcggc                                                              15

<210> SEQ ID NO 105
<211> LENGTH: 15
<212> TYPE: DNA
<213> ORGANISM: Artificial sequence
<220> FEATURE:
<223> OTHER INFORMATION: encoding the 2nd to the 6th amino acid residues
      of TIMs of the recombinant NS1
```

-continued

```
<400> SEQUENCE: 105
accgaagaag cggcg                                              15

<210> SEQ ID NO 106
<211> LENGTH: 15
<212> TYPE: DNA
<213> ORGANISM: Artificial sequence
<220> FEATURE:
<223> OTHER INFORMATION: encoding the 2nd to the 6th amino acid residues
      of TIMs of the recombinant NS1

<400> SEQUENCE: 106
accgaagaag cgggc                                              15

<210> SEQ ID NO 107
<211> LENGTH: 15
<212> TYPE: DNA
<213> ORGANISM: Artificial sequence
<220> FEATURE:
<223> OTHER INFORMATION: encoding the 2nd to the 6th amino acid residues
      of TIMs of the recombinant NS1

<400> SEQUENCE: 107
gcggcggcgg cgggc                                              15

<210> SEQ ID NO 108
<211> LENGTH: 15
<212> TYPE: DNA
<213> ORGANISM: Artificial sequence
<220> FEATURE:
<223> OTHER INFORMATION: encoding the 2nd to the 6th amino acid residues
      of TIMs of the recombinant NS1

<400> SEQUENCE: 108
accgcggcgg cgggc                                              15

<210> SEQ ID NO 109
<211> LENGTH: 15
<212> TYPE: DNA
<213> ORGANISM: Artificial sequence
<220> FEATURE:
<223> OTHER INFORMATION: encoding the 2nd to the 6th amino acid residues
      of TIMs of the recombinant NS1, v refers to not t or none, b
      refers to not a or none, d refers to not c or none, h refers to
      not g or none

<400> SEQUENCE: 109
bddhbbhbbg cgggc                                              15

<210> SEQ ID NO 110
<211> LENGTH: 12
<212> TYPE: DNA
<213> ORGANISM: Artificial sequence
<220> FEATURE:
<223> OTHER INFORMATION: encoding the 2nd to the 5irus

<400> SEQUENCE: 110
accgaagaag gc                                                 12

<210> SEQ ID NO 111
<211> LENGTH: 12
<212> TYPE: DNA
<213> ORGANISM: Artificial sequence
<220> FEATURE:
<223> OTHER INFORMATION: encoding the 2nd to the 5th amino acid residues
      of TIMs of the recombinant NS1
```

-continued

```
<400> SEQUENCE: 111
accgaagaag cg                                                         12

<210> SEQ ID NO 112
<211> LENGTH: 12
<212> TYPE: DNA
<213> ORGANISM: Artificial sequence
<220> FEATURE:
<223> OTHER INFORMATION: encoding the 2nd to the 5th amino acid residues
      of TIMs of the recombinant NS1

<400> SEQUENCE: 112
gcggcggcgg cg                                                         12

<210> SEQ ID NO 113
<211> LENGTH: 12
<212> TYPE: DNA
<213> ORGANISM: Artificial sequence
<220> FEATURE:
<223> OTHER INFORMATION: encoding the 2nd to the 5th amino acid residues
      of TIMs of the recombinant NS1

<400> SEQUENCE: 113
accgcggcgg cg                                                         12

<210> SEQ ID NO 114
<211> LENGTH: 12
<212> TYPE: DNA
<213> ORGANISM: Artificial sequence
<220> FEATURE:
<223> OTHER INFORMATION: encoding the 2nd to the 5th amino acid residues
      of TIMs of the recombinant NS1, v refers to not t or none, b
      refers to not a or none, d refers to not c or none, h refers to
      not g or none

<400> SEQUENCE: 114
bddhbbhbbg cg                                                         12

<210> SEQ ID NO 115
<211> LENGTH: 4
<212> TYPE: PRT
<213> ORGANISM: Artificial sequence
<220> FEATURE:
<223> OTHER INFORMATION: the amino acid residues of TIM of CD40

<400> SEQUENCE: 115

Pro Val Gln Glu
1

<210> SEQ ID NO 116
<211> LENGTH: 4
<212> TYPE: PRT
<213> ORGANISM: Artificial sequence
<220> FEATURE:
<223> OTHER INFORMATION: the amino acid residues of TIM of CD30

<400> SEQUENCE: 116

Ser Val Glu Glu
1

<210> SEQ ID NO 117
<211> LENGTH: 4
<212> TYPE: PRT
<213> ORGANISM: Artificial sequence
<220> FEATURE:
<223> OTHER INFORMATION: the amino acid residues of TIM of 4-1BB
```

-continued

```
<400> SEQUENCE: 117

Ala Ala Gln Glu
1

<210> SEQ ID NO 118
<211> LENGTH: 4
<212> TYPE: PRT
<213> ORGANISM: Artificial sequence
<220> FEATURE:
<223> OTHER INFORMATION: the amino acid residues of TIM of Traid3A

<400> SEQUENCE: 118

Pro Met Gln Glu
1

<210> SEQ ID NO 119
<211> LENGTH: 4
<212> TYPE: PRT
<213> ORGANISM: Artificial sequence
<220> FEATURE:
<223> OTHER INFORMATION: the amino acid residues of TIM of UXT-V1

<400> SEQUENCE: 119

Thr Pro Gln Glu
1

<210> SEQ ID NO 120
<211> LENGTH: 4
<212> TYPE: PRT
<213> ORGANISM: Artificial sequence
<220> FEATURE:
<223> OTHER INFORMATION: the amino acid residues of TIM of LT]R

<400> SEQUENCE: 120

Ile Pro Glu Glu
1

<210> SEQ ID NO 121
<211> LENGTH: 4
<212> TYPE: PRT
<213> ORGANISM: Artificial sequence
<220> FEATURE:
<223> OTHER INFORMATION: the amino acid residues of TIM of MAVS

<400> SEQUENCE: 121

Pro Glu Glu Asn
1

<210> SEQ ID NO 122
<211> LENGTH: 8
<212> TYPE: PRT
<213> ORGANISM: Artificial sequence
<220> FEATURE:
<223> OTHER INFORMATION: the 148th to 154th amino acid residues of NS1
      of A/Puerto Rico/8-SV14/1934 H1N1

<400> SEQUENCE: 122

Arg Ala Phe Thr Glu Glu Gly Ala
1               5

<210> SEQ ID NO 123
<211> LENGTH: 8
<212> TYPE: PRT
<213> ORGANISM: Artificial sequence
<220> FEATURE:
<223> OTHER INFORMATION: the 148th to 154th amino acid residues of NS1
```

```
        of A/Shanghai/P1/2009 H1N1

<400> SEQUENCE: 123

Arg Ala Phe Thr Glu Glu Gly Ala
1               5

<210> SEQ ID NO 124
<211> LENGTH: 8
<212> TYPE: PRT
<213> ORGANISM: Artificial sequence
<220> FEATURE:
<223> OTHER INFORMATION: the 148th to 154th amino acid residues of NS1
        of A/Korea/426/1968 H2N2

<400> SEQUENCE: 124

Arg Ala Phe Thr Glu Glu Gly Ala
1               5

<210> SEQ ID NO 125
<211> LENGTH: 8
<212> TYPE: PRT
<213> ORGANISM: Artificial sequence
<220> FEATURE:
<223> OTHER INFORMATION: the 148th to 154th amino acid residues of NS1
        of A/Taiwan/220/2004 H3N2

<400> SEQUENCE: 125

Arg Ala Phe Thr Glu Glu Gly Ala
1               5

<210> SEQ ID NO 126
<211> LENGTH: 8
<212> TYPE: PRT
<213> ORGANISM: Artificial sequence
<220> FEATURE:
<223> OTHER INFORMATION: the 148th to 154th amino acid residues of NS1
        of A/goose/Czech Republic/1848-K9/2009 H7N9

<400> SEQUENCE: 126

Arg Ala Phe Thr Glu Glu Gly Ala
1               5

<210> SEQ ID NO 127
<211> LENGTH: 8
<212> TYPE: PRT
<213> ORGANISM: Artificial sequence
<220> FEATURE:
<223> OTHER INFORMATION: the 143th to 149th amino acid residues of NS1
        of A/chicken/Oita/1/2011 H5N1

<400> SEQUENCE: 127

Arg Ala Phe Thr Glu Glu Gly Ala
1               5
```

RECOMBINANT NON-STRUCTURAL PROTEIN 1, RECOMBINANT INFLUENZA VIRUS AND IMMUNOLOGICAL COMPOSITION INCLUDING THE SAME, AND METHOD OF TREATING OR PREVENTING DISEASE OR CONDITION CAUSED BY OR ASSOCIATED WITH INFLUENZA VIRUS

RELATED APPLICATIONS

This application is the U.S. national phase under § 371 of International Application No. PCT/CN2020/094471, filed Jun. 4, 2020, which claims benefit of priority from U.S. Provisional Application No. 62/856,760, filed Jun. 4, 2019, the entire contents of each are incorporated by reference.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03 (a)), a Sequence Listing in the form of an ASCII-compliant text file (entitled "Sequence_Listing_3000109-010000_ST25.txt" created on 3 Dec. 2021, and 30,700 bytes in size) is submitted concurrently with the instant application. The entire contents of the Sequence Listing are incorporated herein for reference.

BACKGROUND

Field of Invention

The present invention relates to a recombinant nonstructural protein 1, a recombinant influenza virus, an immunological composition including the same, and a method of treating a disease caused by or associated with an influenza virus. More specifically, the present invention relates to recombinant nonstructural protein 1, a recombinant influenza virus, and an immunological composition including the same, and a method of treating or preventing a disease or condition caused by or associated with an influenza virus in a subject in need thereof.

Description of Related Art

The influenza viruses are members of the family Orthomyxoviridae, and divided into four types of A, B, C and D. Influenza viruses A infect many mammals and avians, and influenza viruses B infect human primarily, the two viruses are the main epidemic viruses of seasonal influenza every year, and influenza viruses A (IVA) and B are the only influenza viruses to cause widespread epidemics in the human population. According to the glycoproteins on the viral surface, hemagglutinin (HA) and neuraminidase (NA), the influenza virus can be further classified into subtypes. To date, 18 different hemagglutinin proteins and 11 different neuraminidase proteins have been found, and different hemagglutinin proteins and different neuraminidase proteins can constitute different subtypes of IVA, for example, H1N1, H3N2, H5N1, and H7N9.

When different virus strains infect the same host, they may exchange part of their genes, recombine, and form new influenza virus strains, resulting in an antigenic shift. New virus strains may have the ability to spread among the human population via gene exchange, thereby introducing new pathogens that the immune system has never seen before, and even cause epidemics of diseases in human society.

The influenza epidemic causes significant economic losses worldwide every year. In the case of the United States, epidemic influenza viruses cause an estimated 8 billion US dollars in medical costs and industrial losses in annual economic loss. To effectively avoid the spread of influenza viruses, the most important thing is epidemic surveillance and vaccine development. As such, for vaccine development, the types of influenza vaccines include several preparations, for example, inactivated influenza vaccines, inactivated influenza split-virus vaccines, live attenuated influenza vaccines, subunit vaccines or purified surface antigen vaccines, and general influenza vaccines. Among these vaccines, live attenuated influenza vaccines can induce a better immune response.

Nonstructural protein (NS1) can inhibit the activation of a host interferon, so that the interferon cannot induce good immune responses. The commercially available live attenuated influenza vaccines attempt to introduce a site mutation into other viral proteins except for NS1, so as to overcome the problem of poor immune responses. However, there are some problems existing in the commercially available live attenuated influenza vaccines as follows. Firstly, the recombinant influenza virus, obtained by introducing a site mutation into other viral proteins except for NS1, has poor replication ability, leading to poor production efficiency of live attenuated influenza vaccines; and the NS1 can still suppress interferon, so that live attenuated influenza vaccines insufficiently induce the immune responses. Moreover, another being-developed vaccine product attempts to completely knock out the NS1 gene of the recombinant virus. Such recombinant virus does not inhibit interferon but has a poor replication ability, so that it is hardly made in mass production.

SUMMARY

In an aspect, the invention provides a recombinant non-structural (NS) protein 1, which at least one amino acid residue is mutated or deleted of the recombinant NS 1 corresponding to 4 contiguous amino acid residues of TRAF3-interacting motifs (TIMs) of NS1 effector domain (ED) of wild-type NS 1.

In yet a further aspect, the invention also provides a recombinant influenza virus comprising the recombinant NS protein 1. The recombinant influenza virus including the NS1 mutant can maintain the comparable replication ability to the wild-type virus, for elevating the interferon activating ability of the subject, inducing better immune response and providing better immunoprotection, thereby being applied in the use for preparation of influenza virus vaccine composition.

In yet a further aspect, the invention also provides an immunological composition, which comprises the aforementioned recombinant influenza virus and a medically available carrier.

In yet a further aspect, the invention also provides a recombinant NS1 protein for use in preparation of an influenza virus vaccine composition.

According to the aforementioned aspect, the invention provides a recombinant nonstructural (NS) protein 1. In an embodiment, at least one amino acid residue can be mutated or deleted of the recombinant NS 1 corresponding to 4 contiguous amino acid residues of TRAF3-interacting motifs (TIMs) of wild-type NS 1, and the $1^{st}$ to the $4^{th}$ amino acid residues of the TIMs of the wild-type NS 1 can comprise an amino acid sequence listed as SEQ ID NO:1. In the aforementioned embodiments, the recombinant NS 1 corresponding to the $1^{st}$ to the $4^{th}$ amino acid residues of the TIMs of the wild-type NS 1 can include but be not limited to an amino acid sequence listed as any one of SEQ ID NOs: 2 to 5.

In another embodiment, at least one amino acid residue can be mutated or deleted of the recombinant NS 1 corresponding to the $1^{st}$ to the $4^{th}$ amino acid residues of TIMs of wild-type NS 1, the $1^{st}$ to the $4^{th}$ amino acid residues of the wild-type NS 1 comprises an amino acid sequence encoded by a nucleic acid sequence listed as SEQ ID NO:6. In the aforementioned embodiments, an amino acid sequence of the recombinant NS protein 1 corresponding to the $1^{st}$ to the $4^{th}$ amino acid residues of TIMs of wild-type NS 1 can be encoded by a nucleic acid sequence selected from the group consisting of any one listed as SEQ ID NOs: 7 to 10.

According to a further aspect, the invention provides a recombinant influenza virus comprising hemagglutinin (HA), neuraminidase (NA), nucleoprotein (NP), matrix (M) protein, polymerase basic protein 1 (PB1), PB2, polymerase acidic protein 1 (PA) and a recombinant NS protein 1, which is characterized that the recombinant NS protein 1 includes any one of the aforementioned amino acid sequences, and at least one amino acid residue of the NP, the M protein, the PB1, the PB2 and the PA protein has site mutation.

In other embodiments, the recombinant influenza virus comprising hemagglutinin (HA), neuraminidase (NA), nucleoprotein (NP), matrix (M) protein, polymerase basic protein 1 (PB1), PB2, polymerase acidic protein 1 (PA) and a recombinant NS protein 1, which is characterized that the recombinant NS protein 1 includes any one of the aforementioned amino acid sequences, at least one amino acid residue of the PB2 and the M protein has at least one site mutation, and the at least one amino acid residue of the NS protein 1 has site mutation except for the aforementioned amino acid sequences. In an example, the recombinant influenza virus can be originated from influenza A virus, for example, but be not limited to H1N1 subtype, H2N2 subtype, H3N2 subtype, H5N1 subtype and/or H7N9 subtype.

According to still another aspect, the invention provides an immunological composition, which comprises any one of the aforementioned recombinant influenza virus and a medically available carrier.

According to a still further aspect, the invention provides a method of treating or preventing a disease or condition caused by or associated with an influenza virus in a subject in need thereof. In the aforementioned embodiment, the subject in need thereof is administered with an influenza virus vaccine composition, the influenza virus vaccine composition comprises an effective dose of recombinant NS1 protein, and the recombinant NS1 protein includes an amino acid sequence as aforementioned.

In the aforementioned embodiment, the influenza virus composition can be an influenza virus attenuated vaccine composition.

With application to the recombinant nonstructural protein 1, the recombinant influenza virus and the immunological composition including the same of the present invention, the recombinant influenza virus including the NS1 mutant can maintain the comparable replication ability to the wild-type virus, for elevating the interferon activating ability of the subject, inducing better immune response and providing better immunoprotection, thereby being applied in the preparation of an influenza virus vaccine composition.

It is to be understood that both the foregoing general description and the following detailed description are by examples, and are intended to provide further explanation of the invention as claimed.

BRIEF DESCRIPTION OF THE DRAWINGS

The disclosure can be more fully understood by reading the following detailed description of the embodiment, with reference made to the accompanying drawings as follows.

DETAILED DESCRIPTION

Figure 1:
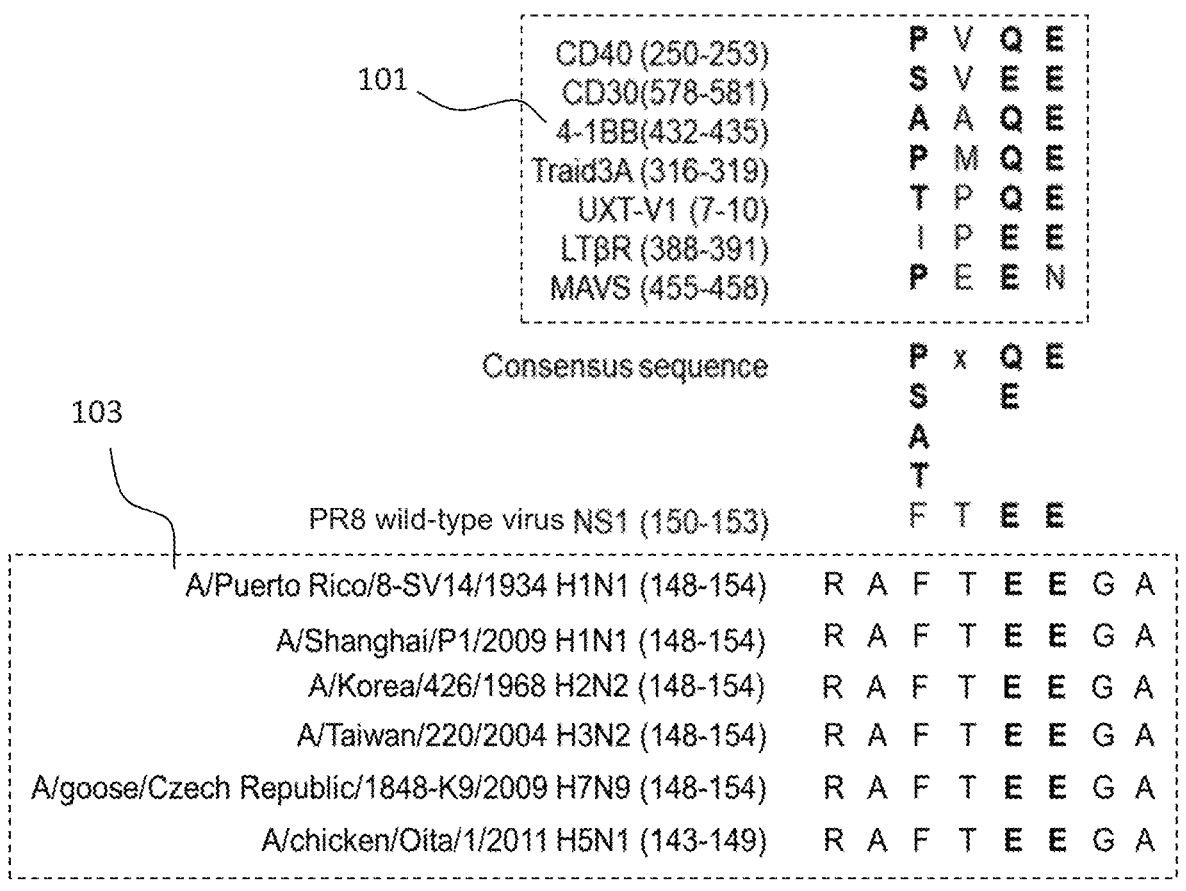
FIG. 1 shows a sequence alignment of TRAF3-interacting motifs (TIMs, as shown in the dotted area 101, see SEQ ID NOs: 115-121) of several proteins and part of NS1 sequence (as shown in the dotted area 103, see SEQ ID NOs: 1 and 122-127) of influenza virus strain according to an embodiment of the invention.

Reference will now be made in detail to the present embodiments of the invention, examples of which are illustrated in the accompanying drawings. Wherever possible, the same reference numbers are used in the drawings and the description to refer to the same or like parts. Where a definition or use of a term in an incorporated reference is inconsistent or contrary to the definition of that term provided herein, the definition of that term provided herein applies and the definition of that term in the reference does not apply.

As aforementioned, the present invention provides a recombinant nonstructural protein 1 (NS1), the recombinant influenza virus and the immunological composition including the same, in which at least one amino acid residue of the TIMs of the recombinant NS1 (also called as NS1 mutant) located at the $1^{st}$ to the $4^{th}$ amino acid residues corresponding to the TRAF3-interacting motifs (TIMs) of effector domain (ED) of wild-type NS1 can be mutated or deleted. The aforementioned TRAF3 refers to TNF receptor-associated factor. In some embodiments, site mutation or deletion can be introduced into at least two contiguous amino acid residues of the 4 contiguous amino acid residues of the TIMs of the recombinant NS1.

The recombinant influenza virus discussed herein refers to the one having the aforementioned recombinant nonstructural protein 1. In the present invention, site mutation or deletion can be introduced into at least one amino acid residue of 4 contiguous amino acid residues of the TIMs of the NS1, the viral replication ability of such recombinant influenza virus can be comparable to the wild-type virus, for elevating the interferon activating ability and inducing better immune response, all of which is confirmed by the following experiments.

Typically, the nonstructural protein 1 can be generally divided into two portions, NS1-RNA binding domain (NS1-RBD) and NS1-effector domain (NS1-ED), respectively. In some embodiments, the recombinant NS1 can be originated from any type of influenza viruses without specific limitation; however, preferably originated from influenza A virus. In the case of influenza A virus, its subtypes can include but be not limited to H1N1 subtype, H2N2 subtype, H3N2 subtype, H5N1 subtype and/or H7N9 subtype.

In some embodiments, the TRAF3-interacting motifs (TIMs) (or called as NS1-TIMs) refers to an amino acid sequence listed as SEQ ID NO:1. Reference is made to FIG. 1, which shows a sequence alignment of TRAF3-interacting motifs (TIMs, as shown in the dotted area 101, see SEQ ID NOs: 115-121) of several known proteins and part of NS1 sequence (as shown in the dotted area 103, see SEQ ID NOs: 1 and 122-127) of PR8 wild-type influenza virus and other influenza viruses. The sequence of TIMs of PR8 wild-type influenza virus is listed as SEQ ID NO: 1, or called as FTEE. Several known signal transducers, for example, MAVS, CD40 and UXT-V1, can interact with TRAF3 via TIMs (sequence including S/T-x-Q/E-E, as shown in the dotted area 101). In addition, according to sequence alignments with other influenza viruses, the $150^{th}$ to $153^{rd}$ amino acid residues of NS1 of wild-type virus (i. e. IAV/PR/8), and partial sequences (as shown in the dotted area 103) of other influenza virus, are common sequences that may be highly conserved and determined in subsequent experiments. It is clarified that, the present invention has determined that TIMs has highly conserved; however, the sequences of influenza viruses are highly variable, and there are the positions of TIMs sequences from different subtypes of influenza virus may be shift slightly. For example, the TIMs of NS1 of the H1N1 subtype, H2N2 subtype, H3N2 subtype and/or H7N9 subtype of influenza A virus can be located at the $150^{th}$ to the $153^{rd}$ amino acid residues corresponding to wild-type NS1. However, in the case of the H5N1 subtype of influenza A virus, its TIMs of NS1 can be located at the $145^{th}$ to the $148^{th}$ amino acid residues corresponding to wild-type NS1. In the cases of other subtypes, the TIMs of NS1 may be located before or after the aforementioned positions. When NS1 of an influenza virus has the sequence listed as SEQ ID NO:2, such sequence can be potential TIMs. That is to say, the actual location of TIMs of NS1 in the present invention is not limited to the aforementioned.

In the present invention, site mutation or deletion can be introduced into at least one amino acid residue of 4 contiguous amino acid residues of the recombinant NS1-TIMs, the viral replication ability of such recombinant influenza virus can be comparable to the wild-type virus, for elevating the interferon activating ability and inducing better immune response. In the cases of the H1N1 subtype, H2N2 subtype, H3N2 subtype and/or H7N9 subtype of influenza A virus, at least one amino acid residue of their TIMs of NS1 located at the $1^{st}$ to the $4^{th}$ amino acid residues corresponding to the TIMs of wild-type NS1 can be mutated or deleted, and the $1^{st}$ to the $4^{th}$ amino acid residues of the TIMs of wild-type NS1 include the amino acid sequence listed as SEQ ID NO:1. In the aforementioned embodiment, the recombinant NS1 located at the $1^{st}$ to the $4^{th}$ amino acid residues corresponding to the TIMs of wild-type NS1 can include but be not limited to any one amino acid sequence listed as SEQ ID NOs: 2-5. In other embodiments, site mutation or deletion can be introduced into at least one amino acid residue of the recombinant NS1 located at the $1^{st}$ to the $4^{th}$ amino acid residues corresponding to the TIMs of wild-type NS1, and the $1^{st}$ to the $4^{th}$ amino acid residues of the TIMs of wild-type NS1 can be encoded by the nucleic acid sequence listed as SEQ ID NO: 6. In the aforementioned embodiment, the recombinant NS1 located at the 1st to the $4^{th}$ amino acid residues corresponding to the TIMs of wild-type NS1 can be encoded by the nucleic acid sequence listed as any one selected from the group consisting of SEQ ID NOs: 7-10.

In some embodiments, the TIMs of the recombinant NS1, mentioned as above, have site mutation or deletion introduced into at least one amino acid residue corresponding to the wild-type NS1-TIMs (listed as SEQ ID NO:1). In certain examples, the recombinant NS1-TIMs can optionally include the sequence corresponding to the wild-type NS1-TIMs (listed as SEQ ID NO:1) and at least one upstream amino acid residue of such sequence. In other examples, the recombinant NS1-TIMs can optionally include the sequence corresponding to the wild-type NS1-TIMs (listed as SEQ ID NO:1) and one or two downstream amino acid residues of such sequence. In other examples, the recombinant NS1-TIMs can optionally include the sequence corresponding to the wild-type NS1-TIMs (listed as SEQ ID NO:1), at least one downstream amino acid residue and/or at least one downstream amino acid residue of such sequence. In other examples, the recombinant NS1-TIMs can optionally include the sequence corresponding to the wild-type NS1-TIMs (listed as SEQ ID NO:1) and least two downstream amino acid residues of such sequence.

In the aforementioned embodiments, in the cases of the H1N1 subtype, H2N2 subtype, H3N2 subtype and/or H7N9 subtype of influenza A virus, the $149^{th}$ to the $155^{th}$ amino acid sequence the recombinant NS1 (corresponding to the $-1$st to the $6^{th}$ amino acid residues of the wild-type NS1-TIMs, totally 7 contiguous amino acid residues) can include but be not limited to any one of the amino acid sequences listed as SEQ ID NOs: 11-22. In another embodiment, the $149^{th}$ to the $154^{th}$ amino acid sequence the recombinant NS1 (corresponding to the $-1^{st}$ to the $5^{th}$ amino acid residues of the wild-type NS1-TIMs, totally 6 contiguous amino acid residues) can include but be not limited to any one of the amino acid sequences listed as SEQ ID NOs: 23-30. In a still another embodiment, the $150^{th}$ to the $155^{th}$ amino acid sequence the recombinant NS1 (corresponding to the $1^{st}$ to the $6^{th}$ amino acid residues of the wild-type NS1-TIMs, totally 6 contiguous amino acid residues) can include but be not limited to any one of the amino acid sequences listed as SEQ ID NOs: 31-38. In a still further embodiment, the $149^{th}$ to the $153^{rd}$ amino acid sequence the recombinant NS1 (corresponding to the $-1^{st}$ to the $4^{th}$ amino acid residues of the wild-type NS1-TIMs, totally 5 contiguous amino acid residues) can include but be not limited to any one of the amino acid sequences listed as SEQ ID NOs: 39-44. In a still another embodiment, the $150^{th}$ to the $154^{th}$ amino acid sequence the recombinant NS1 (corresponding to the $1^{st}$ to the $5^{th}$ amino acid residues of the wild-type NS1-TIMs, totally 5 contiguous amino acid residues) can include but be not limited to any one of the amino acid sequences listed as SEQ ID NOs: 45-50. In other embodiments, the $151^{st}$ to the $155^{th}$ amino acid sequence the recombinant NS1 (corresponding to the $2^{nd}$ to the $6^{th}$ amino acid residues of the wild-type NS1-TIMs, totally 5 contiguous amino acid residues) can include but be not limited to any one of the amino acid sequences listed as SEQ ID NOs: 51-57. In other embodiments, the $151^{st}$ to the $154^{th}$ amino acid sequence the recombinant NS1 (corresponding to the $2^{nd}$ to the $5^{th}$ amino acid residues of the wild-type NS1-TIMs, totally 4 contiguous amino acid residues) can include but be not limited to any one of the amino acid sequences listed as SEQ ID NOs: 58-62.

As such for the several embodiments of the H5N1 subtype, the $144^{th}$ to the $150^{th}$ amino acid sequence the recombinant NS1 (corresponding to the $-1^{st}$ to the $6^{th}$ amino acid residues of the wild-type NS1-TIMs, totally 7 contiguous amino acid residues) can include but be not limited to any one of the amino acid sequences listed as SEQ ID NOs: 11-22. In another embodiment, the $144^{th}$ to the $149^{th}$ amino acid sequence the recombinant NS1 (corresponding to the $-1^{st}$ to the $5^{th}$ amino acid residues of the wild-type NS1-TIMs, totally 6 contiguous amino acid residues) can include but be not limited to any one of the amino acid sequences listed as SEQ ID NOs: 23-30. In a still another embodiment, the $145^{th}$ to the $150^{th}$ amino acid sequence the recombinant NS1 (corresponding to the $1^{st}$ to the $6^{th}$ amino acid residues of the wild-type NS1-TIMs, totally 6 contiguous amino acid residues) can include but be not limited to any one of the amino acid sequences listed as SEQ ID NOs: 31-38. In a still further embodiment, the $144^{th}$ to the $148^{rd}$ amino acid sequence the recombinant NS1 (corresponding to the $-1^{st}$ to the $4^{th}$ amino acid residues of the wild-type NS1-TIMs, totally 5 contiguous amino acid residues) can include but be not limited to any one of the amino acid sequences listed as SEQ ID NOs: 39-44. In a still another embodiment, the $145^{th}$ to the $149^{th}$ amino acid sequence the recombinant NS1 (corresponding to the $1^{st}$ to the $5^{th}$ amino acid residues of the wild-type NS1-TIMs, totally 5 contiguous amino acid residues) can include but be not limited to any one of the amino acid sequences listed as SEQ ID NOs: 45-50. In other embodiments, the $146^{th}$ to the $150^{th}$ amino acid sequence the recombinant NS1 (corresponding to the $2^{nd}$ to the $6^{th}$ amino acid residues of the wild-type NS1-TIMs, totally 5 contiguous amino acid residues) can include but be not limited to any one of the amino acid sequences listed as SEQ ID NOs: 51-57. In other embodiments, the $146^{th}$ to the $149^{th}$ amino acid sequence the recombinant NS1 (corresponding to the $2^{nd}$ to the $5^{th}$ amino acid residues of the wild-type NS1-TIMs, totally 4 contiguous amino acid residues) can include but be not limited to any one of the amino acid sequences listed as SEQ ID NOs: 58-62.

It should be noted that, if mutation or deletion was introduced into the region that is not completely within the contiguous amino acid residues (i.e. 4 contiguous amino acid residues or the $-1^{st}$ to the $6^{th}$ amino acid residues of TIMs of wild-type NS 1), or one or two contiguous mutations or deletions were not introduced into the region, the viral replication ability of such recombinant influenza virus would be hardly compared to the wild-type virus. Such recombinant influenza virus would suppress interferon activation of the subject, leading to poor immune response and immunoprotection.

In some embodiments, a recombinant influenza virus (or called as mutant virus) can be assembled with the aforementioned NS1, hemagglutinin (HA), neuraminidase (NA), nucleoprotein (NP), matrix (M) protein, polymerase basic protein 1 (PB1), PB2, polymerase acidic protein 1 (PA), and the recombinant influenza virus can be produced to an immunological composition, for example, influenza virus vaccine composition. In an example, at least one amino acid residue of NP, M protein, PB1, PB2 and PA of recombinant influenza virus has at least one site mutation, which can be disclosed in flumist or other commercially available products rather than being limited herein. In other examples, the amino acid sequences of NP, M protein, PB1, PB2 and PA can be known sequences or products, for example, at least one amino acid residue of PB2 and M protein has at least one site mutation, and the at least one amino acid residue of the recombinant NS protein 1 has at least one site mutation except for the aforementioned amino acid sequences. In the cases of H1N1 subtype, H2N2 subtype, H3N2 subtype and/or H7N9 subtype, the recombinant NS1 can have site mutations of R38A and K41A; PB2 can have site mutations at 9th, $75^{th}$ and $76^{th}$ amino acid residues; M protein can have site mutations at 36th, $72^{nd}$ and $225^{th}$ amino acid residues, for elevating interferon activation ability of the subject, as disclosed by Du et al. in Science 359:290-296 in 2018, instead of being limited to the recitation herein.

In some embodiments of the aforementioned recombinant viruses, the conventional vectors, for example, the lentiviral vector or other commercially available vectors can bring gene fragments of distinct proteins, co-transfect into cells for preparing the recombinant viruses. In these embodiments, the lentiviral vector for expressing the recombinant NS1 can include nucleic acid sequence listed as SEQ ID NOs: 7 to 10, so as to encode at least one of amino acid sequences of SEQ ID NOs: 2 to 5 of the recombinant NS1.

It should be supplemented that, the recombinant influenza virus including the NS1 mutant can maintain the comparable replication ability to the wild-type virus, for elevating the interferon activating ability of the subject, inducing better immune response, providing better immunoprotection, for improving the conventional problems of poor replication ability, inhibiting interferon and inducing poor immune response of conventionally recombinant influenza virus. Therefore, a method of treating or preventing a disease or condition caused by or associated with an influenza virus in a subject in need thereof can be provided, especially an influenza virus attenuated vaccine composition.

Thereinafter, it will be understood that particular configurations, aspects, examples, clauses and embodiments described hereinafter are shown by way of illustration and not as limitations of the invention. The principal features of this invention can be employed in various embodiments without departing from the scope of the invention. Thus, one skilled in the art can easily ascertain the essential characteristics of the present invention and, without departing from the spirit and scope thereof, can make various changes and modifications of the invention to adapt it to various usages and conditions.

Example 1: Establishment of Evaluation Model

1. Cell Lines

HEK293 and HEK293T cells were described previously. Madin-Darby canine kidney cells (MDCK) were maintained in Dulbecco's Modified Eagle's Medium (DMEM) supplemented with 7% cosmic calf serum (CCS, Hyclone). In addition, for preparing bone marrow-derived dendritic cells (BMDCs), bone marrow cells isolated from 8-12 week old C57BL/6 mice were cultured in Roswell Park Memorial Institute (RPMI) 1640 containing 10% fetal bovine serum (FBS), 20 ng/ml GM-CSF (PeproTech) and 1% antibiotics (containing penicillin and streptomycin). BMDCs were cultured on uncoated cell plates and replaced with fresh medium at Day $3^{rd}$ and $6^{th}$.

2. Reverse Genetics of Influenza Virus

Influenza A/PR/8 viruses were prepared as previously described. The A/Puerto Rico/8/1934 virus used in this EXAMPLE was generated using an eight-plasmid reverse genetics system that was kindly provided by Dr. Webster. The eight plasmids encoded NS1, NP, M protein, PB1, PB2 and PA protein, in which NS1 had an amino acid sequence of SEQ ID NO:48, and at least one amino acid residue of NP, M protein, PB1, PB2 and PA protein had site mutation. Due to the eight-plasmid reverse genetics system of the A/Puerto Rico/8/1934 virus was well understood by the person having ordinary skill in the art rather than reciting its details.

To generate recombinant viruses, eight plasmids were cotransfected into 293T and MDCK cells (cell number ratio of 9:1) by commercial transfection reagent (for example, cationic liposome Lipofectamine® 2000. At 24 hours after transfection, the medium was replaced by serum-free DMEM contain 0.3% BSA. At 72 hours after transfection, the supernatant was collected by centrifugation and viruses were amplified in MDCK cells. The parental A/Puerto Rico/8/1934 influenza virus and the recombinant influenza viruses encoding amino acid sequence listed as SEQ ID NO:2 were propagated in 13-day-old, specific pathogen-free embryonated eggs (Animal Health Research Institute, Tamsui, Taiwan). The virus titer was measured by plaque assay on MDCK cells.

3. Animal Model

C57BL/6 (B6) mice were obtained from the National Laboratory Animal Center. All animal protocols were approved by the Institutional Animal Care and User Committee (NCKU-IACUC-103146, NCKU-IACUC-104082, and NCKU-IACUC-103146) at National Cheng Kung University, and all animal experiments were performed in accordance with the approved guidelines and regulations.

4. Coimmunoprecipitation and Western Blot Analysis

HEK293T cells were transfected with the aforementioned plasmids according to the above methods. 24 hours after transfection, coimmunoprecipitation (Co-IP) and Western Blot (WB) Analysis were performed. Since the Co-IP and WB Analysis were well understood by the person having ordinary skill in the art rather than reciting its details. The antibodies used in the Co-IP and WB Analysis were described later.

5. Nucleic Acids and Plasmids

The products of nucleic acids in EXAMPLES were listed as follows: polyinosinic acid-polycytidylic acid [Poly (I-C)] was purchased from the product Model No. tlrl-pic, Invivo-Gen; 5'-triphosphate double-strand RNA (5'-ppp dsRNA) was purchased from the product Model No. tlrl-3prna, InvivoGen.

The products of plasmids in EXAMPLES were listed as follows: hTLR3-FLAG, FLAG-RIG-I, ΔRIG-I, His-MAVS, IFN—β-Luc, pRL-TK, Flag-TRIF, pcDNA6-Myc-His and IKKi-K38A were conventional plasmids; pSGFP2-C1 (Addgene plasmid 22881) was constructed by Dorus Gadella; pEBG (Addgene plasmid 22227) was constructed by David Baltimor; IKKβ-K44M (Addgene plasmid 11104) was constructed by Dr. A. Raoof of Harvard University; pRK5-HA-K63-Ubiquitin (Addgene plasmid 17606) was constructed by Dr. Ted Dawson of John Hopkins University School of Medicine; Flag-TRAF3 and Flag-TRAF6 were a gift from Karin, M. (Laboratory of Gene Regulation and Signal Transduction, Department of Pharmacology, School of Medicine); Flag-TRAF3 was a gift from Dr. Carl F. Ware (La Jolla Institute for Allergy and Immunology); pHW2000-PR8-PB1, pHW2000-PR8-PB2, pHW2000-PR8-PA, pHW2000-PR8-HA, pHW2000-PR8-NP, pHW2000-PR8-NA, pHW2000-PR8-NS and HW2000-PR8-M1 were gifts from Robert G. Webster (St. Jude Children's Research Hospital, Memphis, TN); nucleic acid fragments of 3×-Flag-RIG-I-CARD (i.e. the $1^{st}$ to the $228^{th}$ amino acid residues) and 3×-Flag-MAVS were amplified by PCR, and then cloned into 3×FLAG-Myc-CMV-26 vector (Sigma); RIG-I-CARD (i.e. the $2^{nd}$ to the $228^{th}$ amino acid residues) was amplified by PCR, and then cloned into pEBG vector; GFP-MAVS was amplified by PCR, and then cloned into psGFP2-C1 vector.

NS full-length fragment of wild-type influenza virus strain A/PR/8 (PR8) was amplified by PCR and cloned into the vector pcDNA6.0/Myc-His (Invitrogen), so as to generate the NS1-Myc-His expression construct with c-terminal tagged Myc-His. Similarly, the NS1-RBD-Myc-His [the $1^{st}$ to the $73^{rd}$ amino acid residues with RNA binding domain (RBD)] and NS1-ED-Myc-His [the $74^{th}$ to the $230^{th}$ amino acid residues of NS1 within the effector domain (ED)] were subjected to PCR cloning. In addition, site mutation was introduced into NS1-ED-C-Myc-His (the $125^{th}$ to the $230^{th}$ amino acid residue), NS1-1-124-Myc-His (the $1^{st}$ to the $124^{th}$ amino acid residue), NS1-E152A/E153A-Myc-His (its NS1 having the sequence listed as SEQ ID NO:2) and pHW2000-PR8-NS-E152A/E153A (its NS1 having the sequence listed as SEQ ID NO:2). The primer pairs cam be designed by variously conventional methods or softwares, rather than reciting their details.

6. Luciferase Reporter Assay

HEK293 cells were cotransfected with a luciferase reporter plasmid (e.g. IFN-β-Luc or ELAM-Luc) and indicated expression constructs. A *Renilla* luciferase-expressing plasmid was used as an internal control to normalize transfection efficiency. An empty vector (pcDNA6.0/Myc-His) was used to equalize the total amount of plasmids. At 16 to 24 hours after transfection or indicated stimulation, cells were lysed with Passive lysis buffer (Promega). The luciferase activities in lysates were measured by the Dual-Luciferase assay (Promega) according to the manufacturer's protocol.

7. In Vivo Ubiquitination Assays

HEK293T cells were transfected as above indicated. N-ethylmaleimide (10 mM) was added to the RIPA lysis buffer [0.5% Deoxycholate, 1% Triton X-100, 25 mM Tris (pH=7.5), 150 mM NaCl, 1 mM EDTA, 0.1% SDS) with protease inhibitors cocktail (Sigma)], and lysates were obtained by centrifugation. For subsequent immunoprecipitation, 1 mg of lysates was incubated with the indicated antibodies for 1 hour at 4° C., 1% Triton X-100 and protein G beads (Pierce) for another 1 hour at 4° C. The beads were washed 4 times with RIPA lysis buffer (with protease inhibitors) and then boiled with 6×SDS containing sample buffer at 75° C. for 5 minutes to elute the proteins.

8. Plaque Assay

The standard plaque assay was performed to determine influenza virus titer. Briefly, the 6-well plate was seeded with approximately $6 \times 10^5$ MDCK cells per well for at least 16 h to allow cell attachment. Before virus infection, the cell monolayer was washed with 1×dPBS (Dulbecco's phosphate-buffered saline) and 2×DMEM (Dulbecco's modified eagle medium), respectively. Each well was incubated with 200 µL of the serial 10-fold diluted virus-containing samples for 1 hour incubation. The plates were shaken every 15 minutes during the incubation period. After 1 hour, the virus-containing supernatants were removed and the cells were washed by 1×dPBS to remove the unattached virus. Then, 2 mL of 1.6% sterile agarose mixed with equal volume 2×DMEM was added into the cell monolayer and incubated at 37° C. for 72 hours. When the plaques were formed, the DMEM-containing agarose was removed and the cells were fixed with 4% paraformaldehyde and stained with crystal violet for 30 minutes. Then the plates were washed and air dried at room temperature. Then the plaque numbers were counted in duplicate and the viral titers were calculated.

9. Confocal Microscopy

For immunofluorescence, cells were fixed with 4% paraformaldehyde (PFA) in PBS for 15 min followed by permeabilization with 0.2% Triton X-100 for 10 minutes. Cells were washed with PBS (pH 7.2-7.4) and blocked with 0.1% BSA in PBST (phosphate-buffered saline with Tween 20). Primary antibodies included anti-TRAF3 antibody (sc-948, Santa Cruz; 1:50 dilution) and anti-Myc antibody (clone 4A6, Millipore; 1:1000 dilution). Secondary antibodies included fluorophore-conjugated secondary antibody (Alexa Fluor®488 and 564, Abcam; 1:500 dilution in PBS 0.1% BSA). The nucleus was revealed by 4',6-diamidino-2-phenylindole (DAPI) staining. The confocal micrographs represented a single optical section through the plane of the cell. Images were acquired with FV10-ASW on an FV1000 inverted microscope (OLYMPUS, Japan) with a 60×, PLAPO, NA: 1.4, WD: 0.15, Oil disc lens.

10. RNA Isolation and Reverse Transcription-Polymerase Chain Reaction (RT-PCR)

Total RNAs were isolated by using RNAzol according to the manufacturer's protocol. cDNA was prepared by using a high-capacity cDNA reverse transcription kit (Applied Biosystems).

11. Evaluation of Interaction of NS1 with Viral RNA

HEK293T cells in a 10-cm dish were transfected with 15 µg of pcDNA-NS1-Myc-His, pcDNA-NS1-RBD-Myc-His or pcDNA-NS1-ED-Myc-His plasmids using Lipofectamine 2000. After 24 hours post-transfection, cells were lysed in RIPA buffer (Tris 50 mM, NaCl 150 mM, 0.5% sodium deoxycholate, 1% Triton X 100, 0.1% SDS) with protease inhibitor. Insoluble ingredients were removed by centrifugation. Cell lysate was purified by Nickle beads (25 µL bed volume) (GE Healthcare Life Sciences) in base buffer [20 mM Hepes pH 7.9, 2 mM EDTA, 15% Glycerol and 0.05% NP40, 50 mM NaCl, 10 µg/mL each of aprotinin and pepstatin, 0.5 mM PMSF, 2 mM DTT and 1× ProtectRNA™ RNase Inhibitor (#R7397, Sigma)] for 1 hour at 4° C. The beads were washed with the base buffer and incubated with 10 µg of total RNA from recombinant influenza virus-infected HEK293 cells for another 1 hours at 4° C. to pulldown RNA. The beads were washed 3 times with base buffer to remove the non-specific RNA. Then, RNA was sequentially isolated from the beads by adding RNAzol as previously described. Isolated RNA was reversed transcribed by RT-PCR and determined the RNA amount of NS1 and mutant virus.

12. Enzyme-Linked Immunosorbent Assay (ELISA)

IL-6 and IFN-β were measured for supernatants obtained from recombinant virus infected mouse's conventional dendritic cells (cDCs) by ELISA. ELISA kits were shown as follows: mouse IL-6 (eBioscience), mouse RANTES (R & D Systems) and mouse IFN-β (InvivoGen Lumikine Xpress™ mIFN-β). Values represented the mean±standard error of the mean (S.E.) of duplicated samples. Data are representative of two or three experiments.

13. Propagation of IAV in Cell Culture and Embryonated Chicken Eggs

The influenza A/PR/8/34 wild-type virus and recombinant virus carrying NS1 mutations (encoding amino acid sequence listed as SEQ ID NO:2) were generated using an eight-plasmid reverse genetics system. To generate recombinant influenza virus, plasmids encoding NS WT (pHW2000-PR8-NS) and NS mutant virus (pHW2000-PR8-NS E152A/E153A encoding amino acid sequence listed as SEQ ID NO:2) were co-transfected with other seven expression plasmids (pHW2000-PR8-PB1, pHW2000-PR8-PB2, pHW2000-PR8-PA, pHW2000-PR8-HA, pHW2000-PR8-NP, pHW2000-PR8-NA, and pHW2000-PR8-M1) into co-cultured 293T/MDCK cells in 60 mm dish by using Lipofectamine™ 2000 (Invitrogen). After 24 hours of post-transfection, the medium was replaced with 2 mL of DMEM with 0.3% BSA containing 1 µg/mL of N-p-tosyl-L-phenyl-alanine chloromethyl ketone (TPCK)-Trypsin. At 72 hours post-infection, the supernatants were collected by centrifugation. Wild-type virus (IAV/PR8) or recombinant virus (IAV/PR8) carrying the NS1 mutant gene (encoding amino acid sequence listed as SEQ ID NO:2) were further propagated in 10-days-old, specific pathogen-free (SPF) embryonated chicken eggs. The infected eggs were incubated at 35° C. and approximately 60% humidity for 48 hours. All procedures were performed under sterile conditions. Prior to harvesting the allantoic fluid, the chicken eggs were incubated overnight at 4° C. for the coagulation of embryo's blood leading it to death. Then the allantoic fluid was centrifuged and transferred to a fresh microtube. Ultimately, the virus treated allantoic fluid was stocked at −80° C. freezer for long-term storage.

14. Virus Infects Mice

C57BL/6 mice on average 6-7 weeks old were anesthetized and intraperitoneal injected with the mixture of Zoletil® 50 (50 mg/mL) and Rompun®. 20 µL of serum-free DMEM (including wild-type influenza virus (IAV/PR8) and NS1 mutant virus (NS1 E152A/E153A, IAV/PR8, encoding amino acid sequence listed as SEQ ID NO:2) infected the anesthetized mice. Within 14 days, the body weight of the mice were measured every day, and statistically assessed by two-way ANOVA for weight loss data. In this EXAMPLE, if a mouse had 15% loss in body weight, it would be considered as a potential parameter for human endpoint decision, and such mouse would be sacrificed. The statistical analyses were performed using Log-rank (Mantel-Cox) test, and probable survival curve could be estimated using Kaplan-Meier curves. Viral titer in lung from two different genotypes of mice could be analyzed using Mann Whitney test.

15. Growth Kinetics of Influenza Viruses

MDCK cells in 24-well cell plate were infected with a dose of multiplicity of infection (MOI) 0.01 of wild-type influenza virus (IAV-WT) or NS1 mutant virus (encoding amino acid sequence listed as SEQ ID NO:2). At given time points (24, 48, 72 hours), the cell supernatant were collected, and infectious virions were assessed using plaque assay on MDCK cells.

16. Statistical Analysis

Statistical analyses of the above EXAMPLES were performed using unpaired, two-tailed, Student's t-tests available in GraphPad Prism software (La Jolla, CA, USA). Kaplan-Meier analysis available in GraphPad Prism software (La Jolla, CA, USA) was used for analyzing survival data. Two-way ANOVA available in GraphPad Prism software (La Jolla, CA, USA) for analyzing weight loss data. The P value below 0.05 (*), 0.005 () or 0.0005 (*) was considered to be statistically significant. The levels of statistical significance were expressed as p-values, *, $p<0.05$; , $p<0.005$; *, $p<0.0005$; NS: non-significant.

Figure 2A:
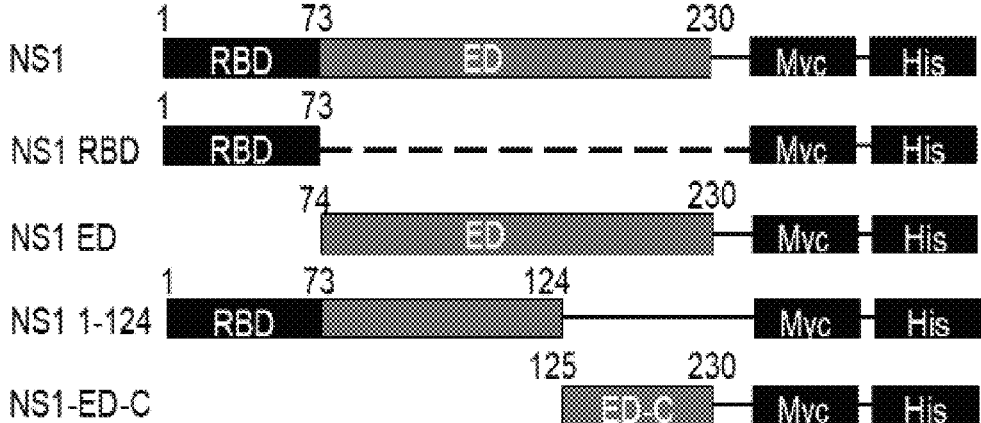
FIG. 2A shows a schematic diagram of partial genes of several expressions constructs of NS1 mutant according to several embodiments of the invention.
Figure 2B:
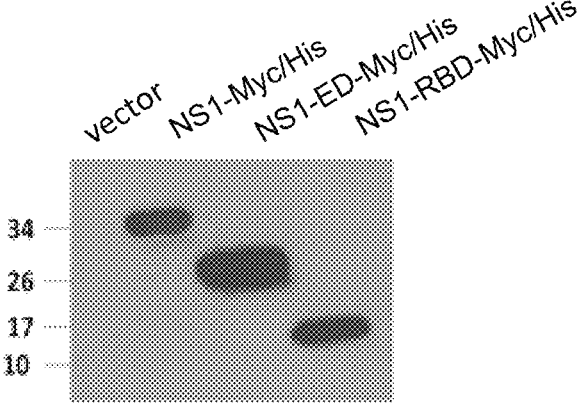
FIGS. 2B to 2I show bar diagrams of promoter activity and western blot analyses of RIG-I signaling to the Type I IFN induction via RBD and ED of NS1 mutant according to several embodiments of the present invention.
Figure 2C:
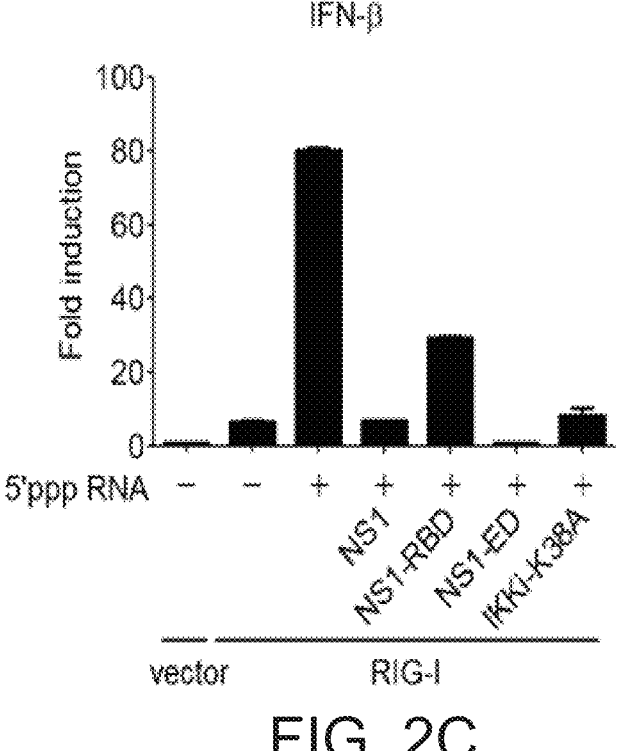
Figure 2D:
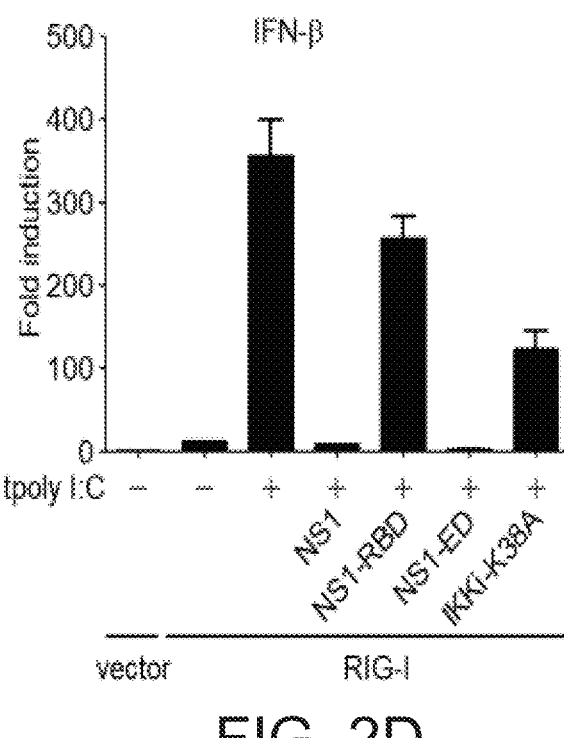
Figure 2E:
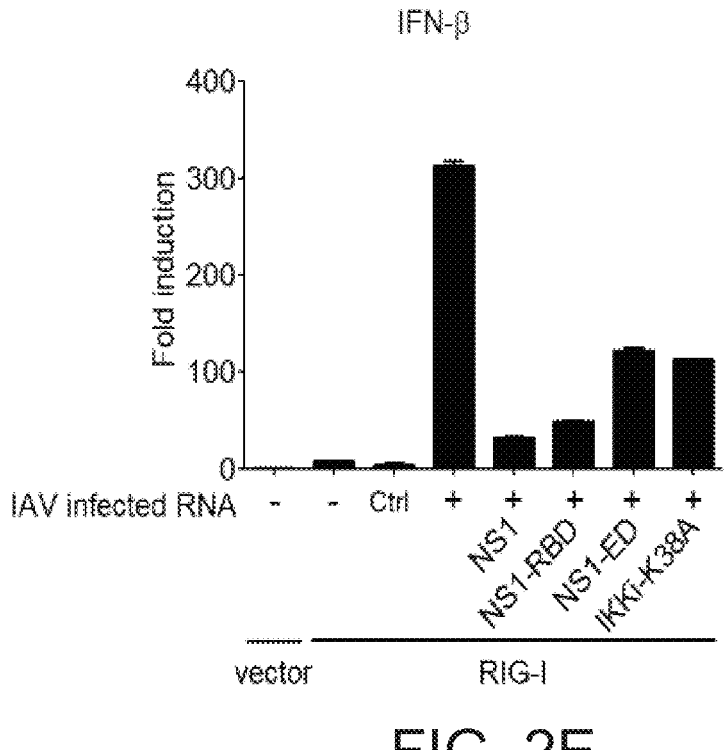
Figure 2F:
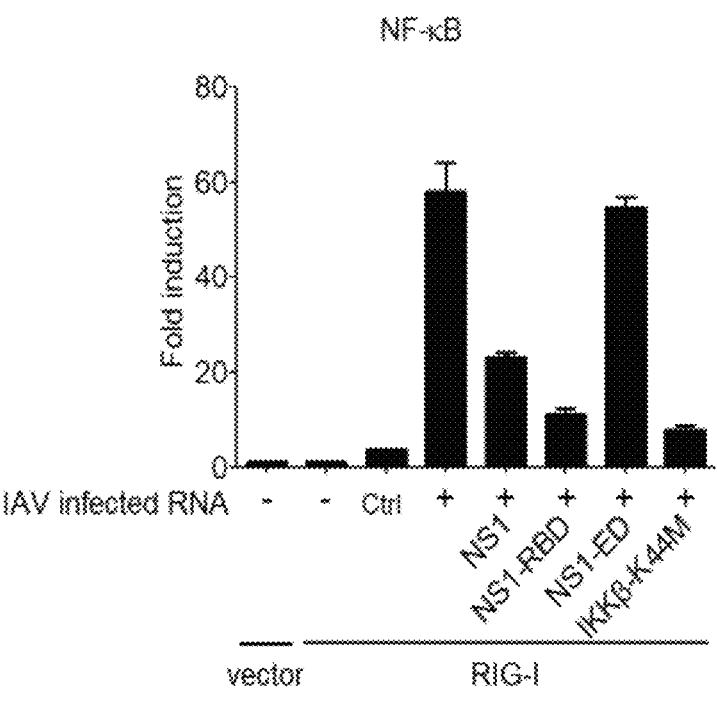

Example 2. Evaluation of Mechanism, Effectiveness and Safety of Recombinant NS1 and Recombinant Influenza Virus 1. NS1 Mutant could Activate the Type1 IFN without Binding RNA Several NS1 expression constructs were shown in FIG. 2A, for assessing the effect of RIG-I signaling to the Type I IFN induction via RBD and ED, and the results were shown in FIGS. 2B to 2I.

Reference was made to FIGS. 2B to 2I, which showed bar diagrams of promoter activity and western blot analyses of RIG-I signaling to the Type I IFN induction via RBD and ED of NS1 mutant according to several embodiments of the present invention.

As shown in the results of in vitro RNA binding experiments of FIGS. 2B to 2F, NS1-RBD could compete with RIG-I to bind viral RNA, leading in influencing IFN-β and NF-κB pathways. However, NS1-ED primarily targeted RIG-I-IFN-β axis via an RNA binding-independent mechanism.

Figure 2G:
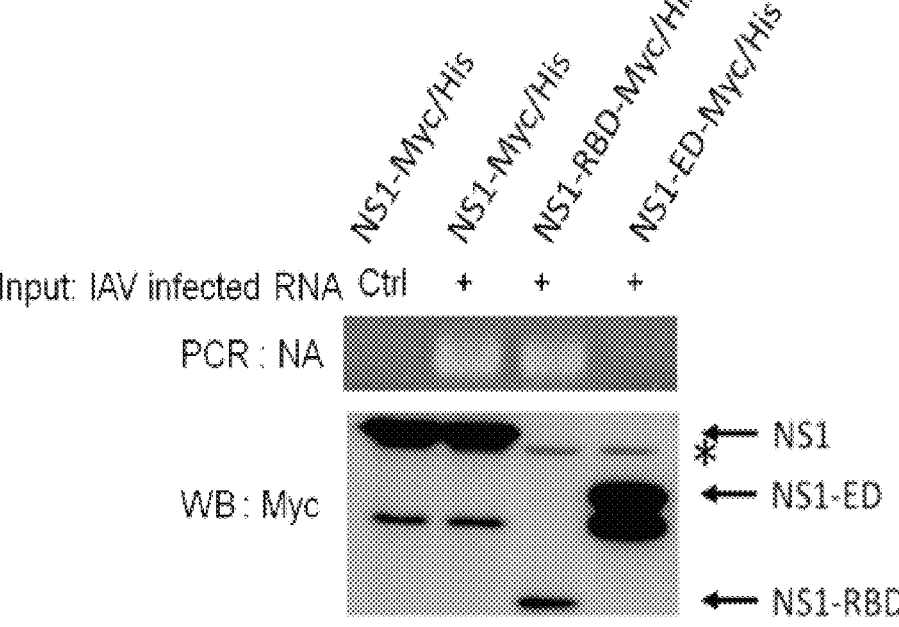
Figure 2H:
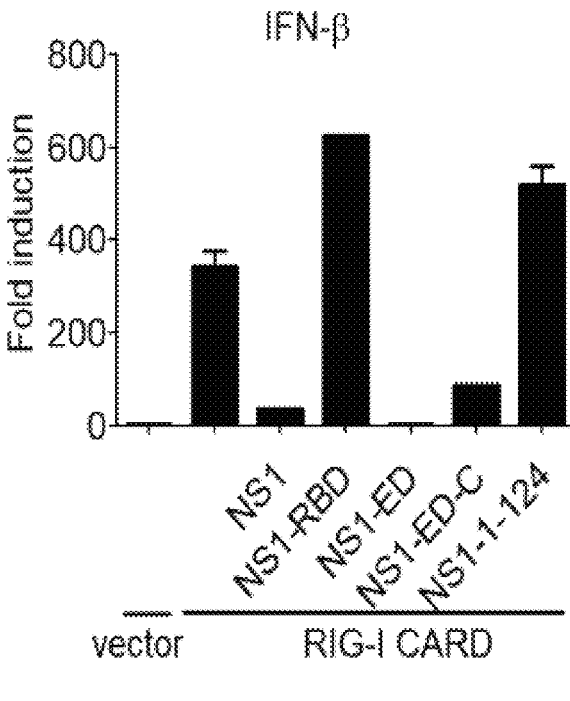
Figure 2I:
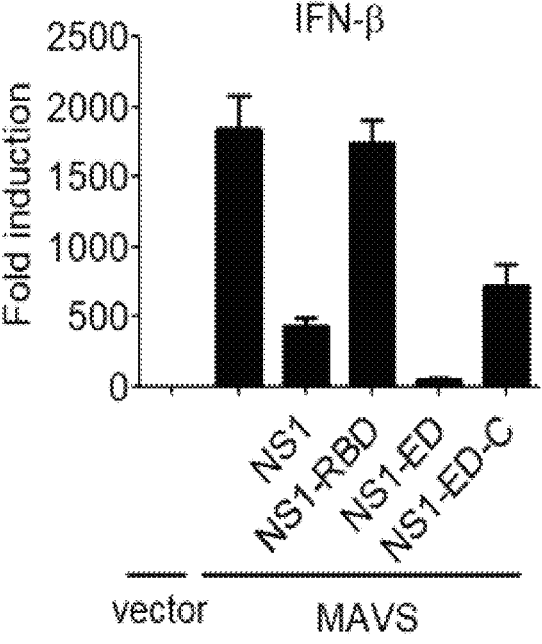

As shown in the results of in vitro RNA binding experiments of FIGS. 2G to 2I, NS1-ED did not bind to viral RNA, but it could antagonize RIG-I signaling to type I IFN activation. To that end, a RIG-I active mutant (called RIG-I CARD) was used for evaluation, the C-terminal region for NS1-ED (a. a. 125-230 of NS1) was shown to block IFN-β promoter activation, implying that NS1-mediated immune evasion via its distal C-terminal effector domain to target the RIG-I-IFN-β axis.

2. NS1 Mutant Binding to TRAF3 for Selectively Activating IFN

Figure 3A:
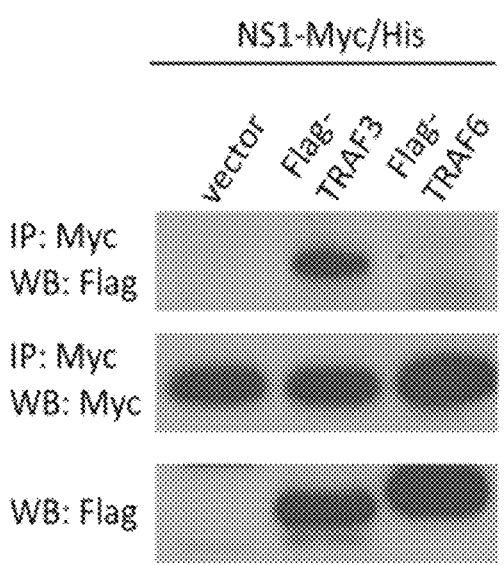
FIGS. 3A to 3C show co-IP-WB results of several NS1-ED mutants according to several embodiments of the present invention.
Figure 3B:
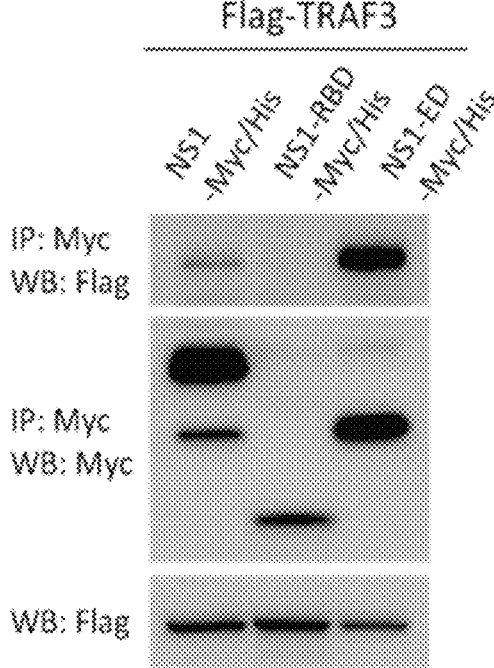
Figure 3C:
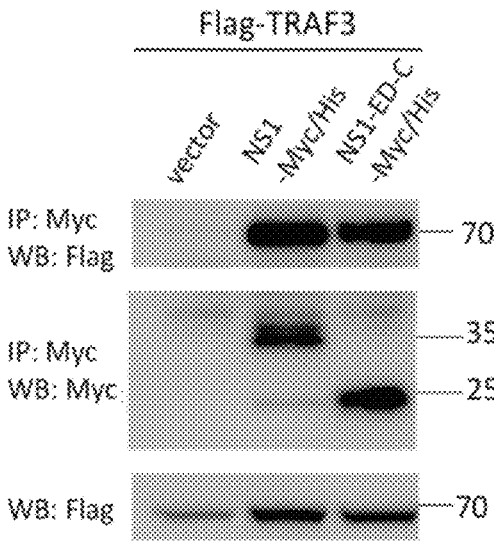

Reference was made to FIGS. 3A to 3C, which showed co-IP-WB results of several NS1-ED mutants according to several embodiments of the present invention. As shown in the result of HEK293T cell experiments of FIG. 3A, wild-type NS1 (NS1-Myc/His) could bind to TRAF3 rather than TRAF6. As shown in the results of HEK293T cell experiments of FIGS. 3b and 3c, NS1-ED and NS1-ED-C could also bind to TRAF3, suggesting that the C-terminal region of NS1 was essential for binding to TRAF3.

Figure 3D:
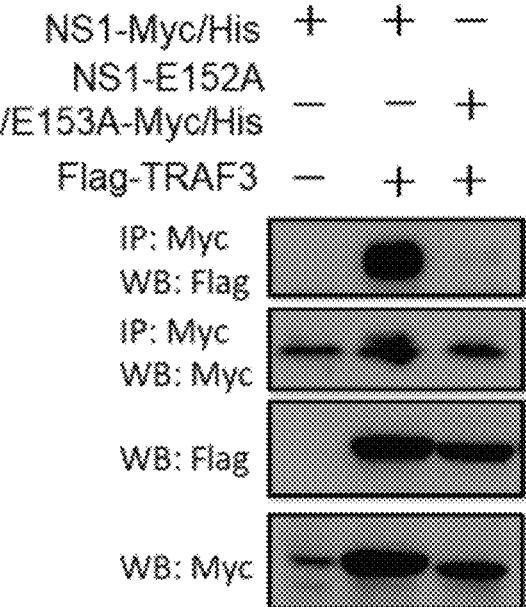
FIG. 3D shows the co-IP-WB result of HEK293 cells transfected with NS1 mutant virus or wild-type virus according to an embodiment of the present invention.

Reference was made to FIG. 3D, which showed the co-IP-WB result of HEK293 cells transfected with NS1 mutant virus or wild-type virus according to an embodiment of the present invention. As further shown in the result of FIG. 3D, NS1 mutant virus (NS1-E152A/E153A-Myc/His, encoding SEQ ID NO:2) failed to bind TRAF3.

Figure 4A:
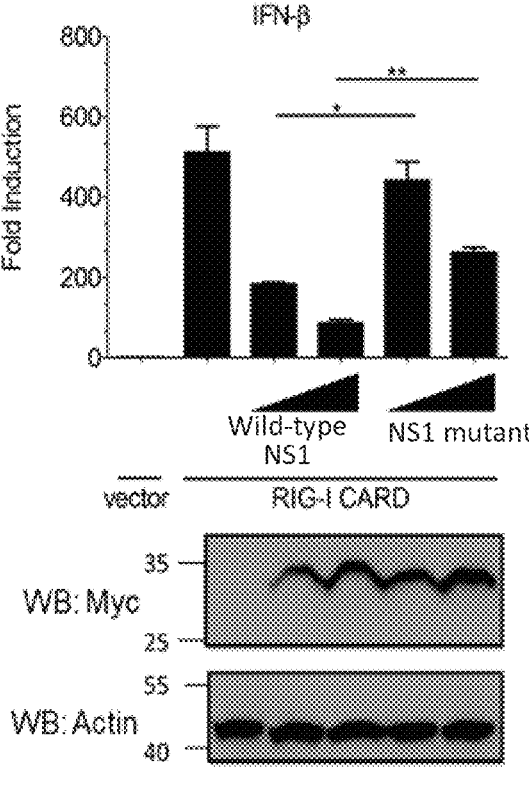
FIGS. 4A and 4B respectively show the result of IFN-β promoter activation induced by RIG-I-CARD (FIG. 4A) or MAVS (FIG. 4B) of HEK293 cells transfected with NS1 mutant virus or wild-type virus according to an embodiment of the present invention.
Figure 4B:
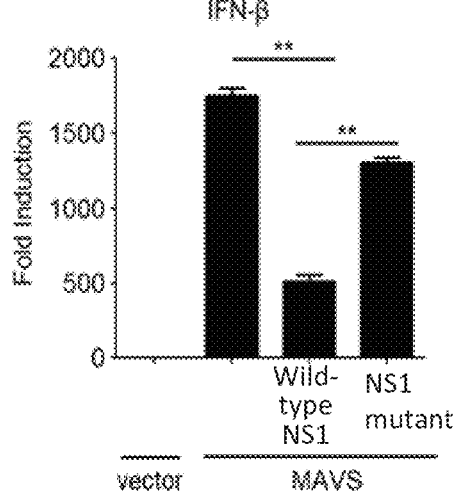

Reference was made to FIGS. 4A and 4B, which respectively showed the result of IFN-β promoter activation induced by RIG-I-CARD (FIG. 4A) or MAVS (FIG. 4B) of HEK293 cells transfected with NS1 mutant virus or wild-type virus according to an embodiment of the present invention. As further shown in the result of FIG. 4A, based on the same protein expression level between wild-type virus and NS1 mutant virus (encoding SEQ ID NO:2) (as shown in the lowest panel of FIG. 4A), compared to wild-type NS1 blocking the IFN-β activation induced by RIG-I CARD, the NS1 mutant (encoding SEQ ID NO:2) diminished the ability to block the IFN-β activation (as shown in the upper panel of FIG. 4A). Similar result could be also shown in the result of the IFN-β activation induced by MAVS (as shown in FIG. 4B).

Figure 5A:
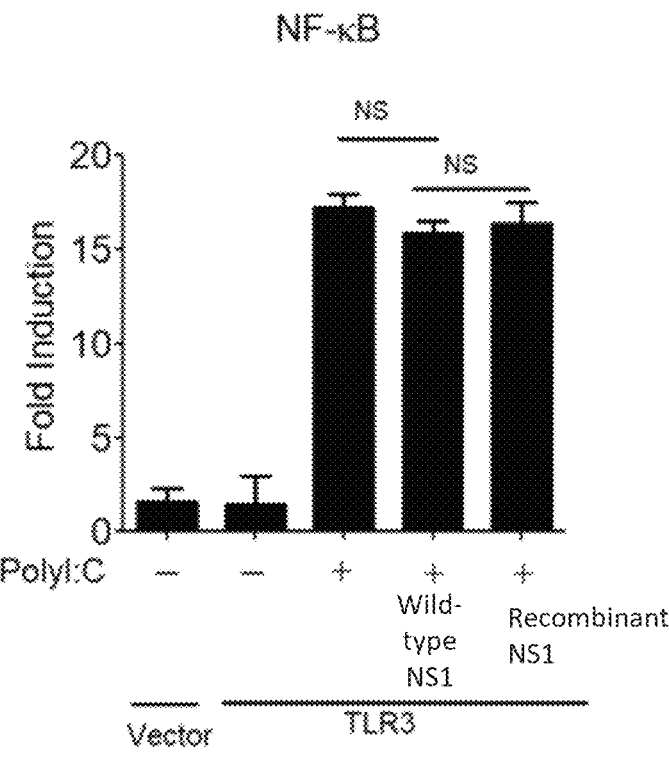
FIGS. 5A and 5B respectively show the results of NF-κB promoter (FIG. 5A) or IFN-β promoter (FIG. 5B) activation of HEK293 cells containing other vector or not, transfected with NS1 mutant (encoding SEQ ID NO:2) or wild-type NS1, together with pELAM-Luc and empty vector or TLR3 according to an embodiment of the present invention.
Figure 5B:
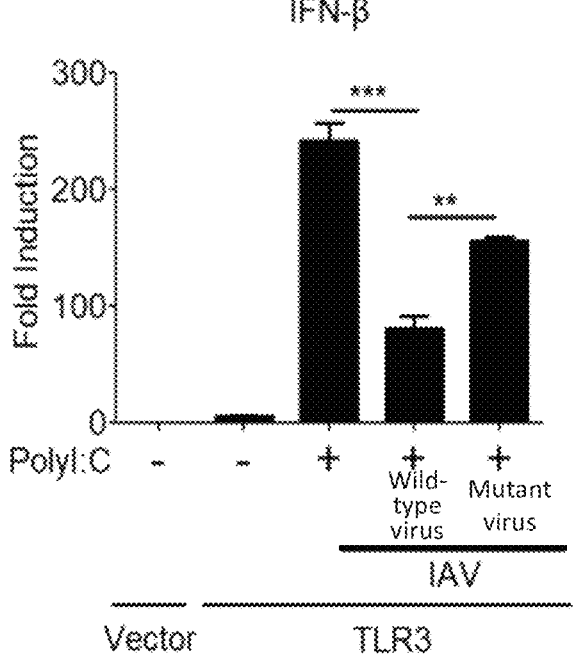

Reference was made to FIGS. 5a and 5b, which respectively showed the results of NF-κB promoter (FIG. 5A) or IFN-β promoter (FIG. 5B) activation of HEK293 cells containing other vector or not, transfected with NS1 mutant (encoding SEQ ID NO:2) or wild-type NS1, together with pELAM-Luc and empty vector or TLR3 according to an embodiment of the present invention.

In FIG. 5A, HEK293 cells were co-transfected with wild-type NS1, NS1 mutant (encoding SEQ ID NO:2) together with pELAM-Luc and empty vector or TLR3, in the treatment of poly I:C (20 μg/mL) or not. After 24 hours, the transfected cells were left untreated or treated with poly I:C (20 μg/mL). After another 16 hours, treated cells were harvested for analyzing the IFN-β promoter activity. As shown in the result of FIG. 5A, neither wild-type NS1 nor NS1 mutant blocked TLR3 signaling to the NF-κB promoter, and these data demonstrated that wild-type NS1 (or called as NS1-TIM) merely targeted the TLR3-TRAF3-IFN-β axis.

In FIG. 5B, HEK293 cells were co-transfected with IFN-β-Luc and empty vector or TLR3. After 16 hours, the transfected cells were infected with NS1 WT virus (PR8, 0.2 MOI) or NS1 mutant virus (encoding SEQ ID NO:2, PR8, 0.2 MOI). After 12 h, transfected HEK293 cells were left untreated or treated with poly I:C (1 μg/mL). After another 12 h, treated cells were harvested for analyzing the IFN-β promoter activity. As shown in the result of cells infected by viruses in FIG. 5B, NS1 wild-type virus could blocked IFN-β promoter activation, whereas the NS1 mutant virus (encoding SEQ ID NO:2) reduced this blocking effect that showed the similar result to FIG. 4A.

Figures 5C, 5D:
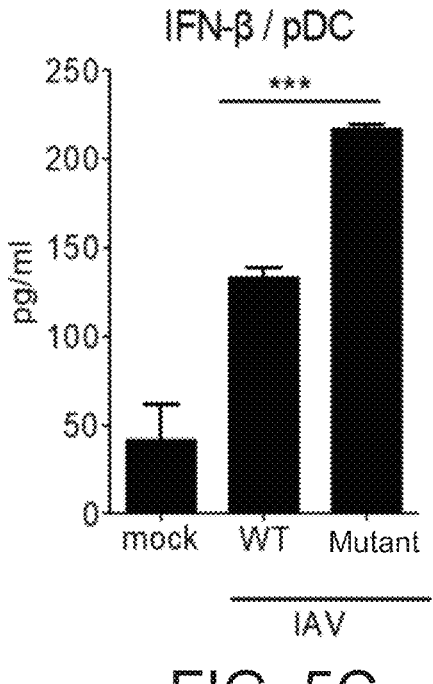
FIG. 5C shows the result of IFN-β expression level of bone marrow-derived plasmacytoid dendritic cells (pDCs) infected with NS1 mutant (encoding SEQ ID NO: 2) or wild-type NS1 according to an embodiment of the present invention.
FIG. 5D shows the bar diagram of the promoter activation of RIG-I signaling to type I IFN induction via TIMs of several NS1 mutant viruses according to another embodiment of the present invention.

Reference was made to FIG. 5C, which showed the result of IFN-β expression level of bone marrow-derived plasmacytoid dendritic cells (pDCs) infected with NS1 mutant (encoding SEQ ID NO:2) or wild-type NS1 according to an embodiment of the present invention. In FIG. 5C, bone marrow-derived plasmacytoid dendritic cells (pDCs) were infected with wild-type NS1 virus (PR8, 10 MOI) or NS1 mutant virus (encoding SEQ ID NO:2, PR8, 10 MOI) for 24 hours, IFN-β expression level (pg/mL) could be analyzed by ELISA. Values represent the mean±SD of triplicate samples. *P<0.05, P<0.005, *P<0.0005, and NS stands for "not significant" statistically using unpaired t-tests. As shown in the result of pDCs cells infected by viruses in FIG. 5C, wild-type NS1 virus, but not NS1 mutant virus, could suppress TLR7 induced type IIFN activation. Therefore, NS1 mutant virus could induce more IFN-β expression level.

Reference was made to FIG. 5D, which showed the bar diagram of the promoter activation of RIG-I signaling to type I IFN induction via TIMs of several NS1 mutant viruses according to another embodiment of the present invention. FIG. 5D was performed using "6. luciferase reporter gene assay of EXAMPLE 1". The wild-type virus encoded SEQ ID NO:1, the mutant virus 1 encoded SEQ ID NO: 2, the mutant virus 2 encoded SEQ ID NO:3, the mutant virus 3 encoded SEQ ID NO: 4. During the experiment, HEK293 cells were cultured in the 48-well cell plate, wild-type virus or NS1 mutant virus, or plasmid DNA (30 ng or 60 ng for each well) of NS1 mutant virus, were added into each well. The induction folds of luciferase activity can assess the promoter activation of RIG-I signaling to type I IFN induction via NS1 mutant virus. As shown in the result of FIG. 5D, in the transfection dose of 60 ng/well, NS1 mutant virus less suppress IFN activation of the tested cells compared to wild-type NS1 virus. Moreover, as the changing degree of TIMs sequence increases (e.g. mutant virus 2 and mutant virus 3), the mutant viruses much less suppressed IFN activation of the tested cells, as well as increased IFN activation of the tested cells.

3. Evaluation of Propagation Ability of Recombinant Influenza Viruses

Figure 6:
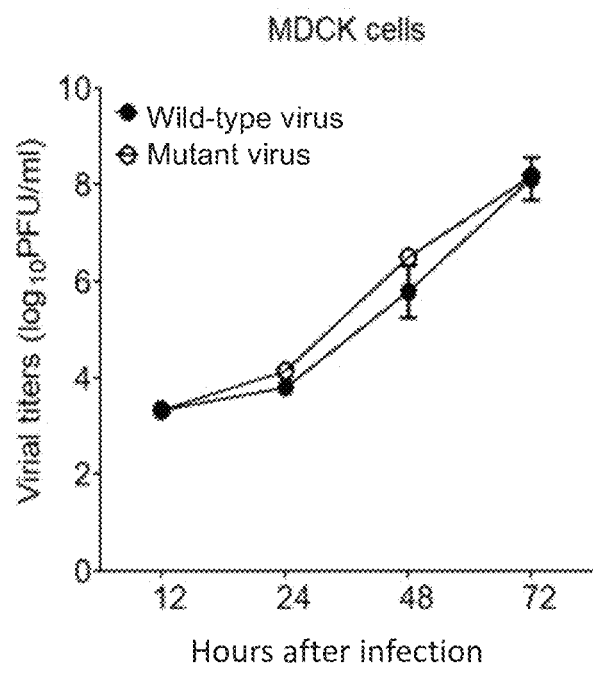
FIG. 6 shows the growth curve of the wild-type NS1 virus (IAV/PR8) or NS1 mutant virus according to an embodiment of the present invention.

MDCK cells were infected with MOI 0.1 of wild-type NS1 virus (IAV/PR8) or NS1 mutant virus (encoding SEQ ID NO:2), the supernatants were harvested at given time points, the amount of infectious virions in the supernatant could be analyzed by the plaque assay, for obtaining the growth curve, and the result was shown in FIG. 6.

Reference was made to FIG. 6, which showed the growth curve of the wild-type NS1 virus (IAV/PR8) or NS1 mutant virus according to an embodiment of the present invention. As shown in the result of FIG. 6, there was no significant difference between the growth curve of the NS1 mutant virus (encoding SEQ ID NO: 2) and the wild-type NS1 virus, showing that the NS1 mutant virus had comparable replication ability to the wild-type NS1 virus.

4. Evaluation of Safety and Immunoprotection of Recombinant Influenza Virus

Figure 7:
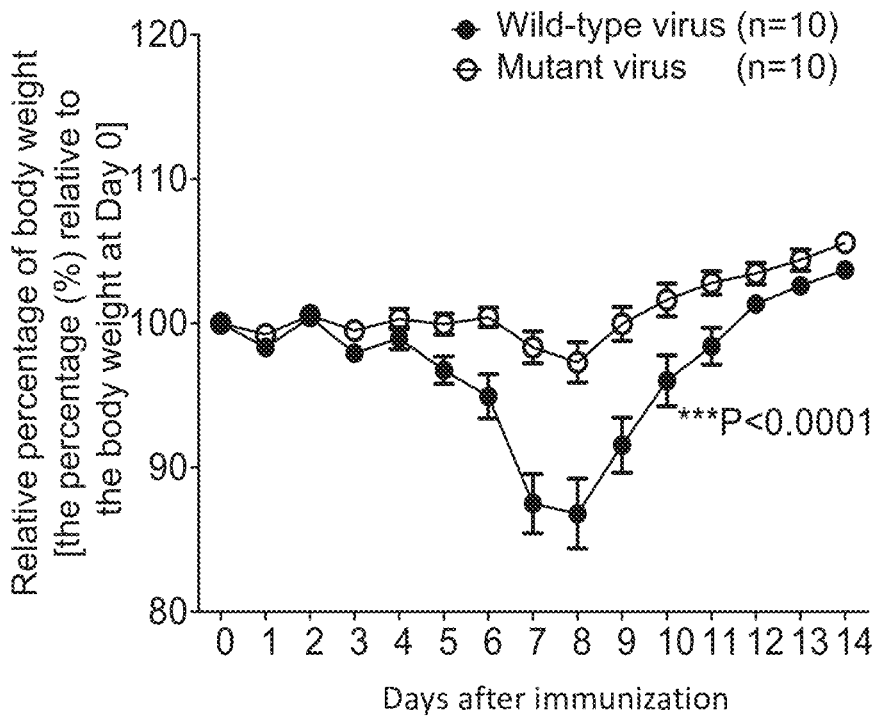
FIG. 7 shows the curve diagram of daily percentage changes of body weight of mice administered with the mutant virus or the wild-type virus according to an embodiment of the present invention.

Reference was made to FIG. 7, which showed the curve diagram of daily percentage changes of body weight of mice administered with the mutant virus or the wild-type virus according to an embodiment of the present invention. Firstly, 6-7 week-old mice were divided into several groups, 10 animals per group, each animal infected intranasally (i.n.) with a dose of 50 PFU of wild-type NS1 virus (IAV/PR8) or NS1 mutant virus (IAV/PR8, encoding amino acid sequence of NS1 listed as SEQ ID NO:2). Body weights of mice were monitored daily for 14 days, and the result was shown in FIG. 7.

As shown in the result of FIG. 7, there was no significant difference in the body weights of mice infected intranasally (i.n.) with NS1 mutant virus (encoding amino acid sequence listed as SEQ ID NO:2), suggesting that NS1 mutant virus had less toxicity and reduced pathogenicity in vivo. In comparison, the body weights of mice infected intranasally (i.n.) with wild-type NS1 virus (IAV/PR8) had significant loss, especially 6-9 days after intranasal infection, the body weight loss was more significant, demonstrating that the wild-type NS1 virus had more toxicity and higher pathogenicity in vivo.

Figure 8:
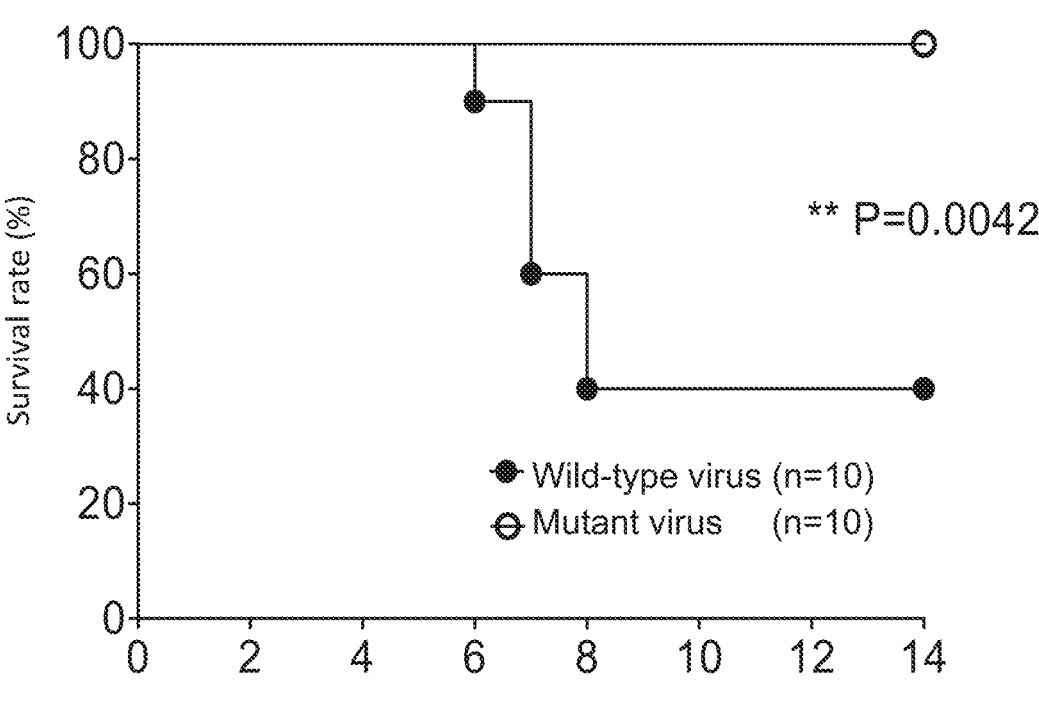
FIG. 8 shows a line diagram of the individual survival rate of mice administered with the mutant virus or the wild-type virus over time according to an embodiment of the present invention.

In addition, reference was made to FIG. 8, which showed a line diagram of the individual survival rate of mice administered with the mutant virus or the wild-type virus over time according to an embodiment of the present invention.

As shown in the result of FIG. 8, there was no death in the mice infected intranasally (i.n.) with NS1 mutant virus (encoding amino acid sequence listed as SEQ ID NO:2) for 14 days of the experiment period, the survival rate was 100%, leading to better survival rate and higher safety. In comparison, 6-8 days after the intranasal (i.n.) infection of mice with wild-type NS1 virus (IAV/PR8), the mice died one after another, the survival rate was merely 40%, demonstrating that the wild-type NS1 virus had less safety.

Figure 9:
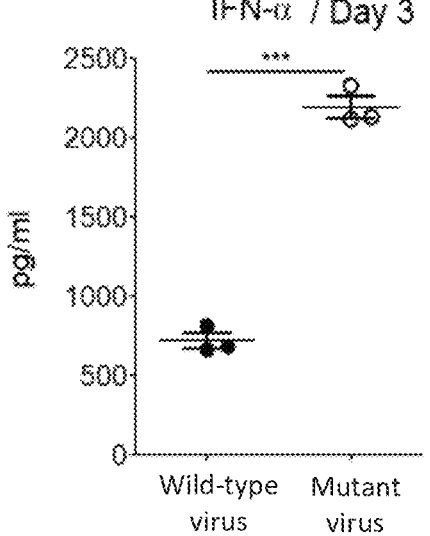
FIG. 9 shows a scatter graph of IFN-α amount (pg/mL) in the lung of mice after 3 days administration with the mutant virus (IAV/PR8) or the wild-type virus (IAV/PR8) according to an embodiment of the present invention.

6-7 week-old mice were divided into 3 or 4 animals per group, infected intranasally (i.n.) with a dose of 50 PFU of wild-type NS1 virus (IAV/PR8) or NS1 mutant virus (IAV/PR8). IFN-α production in the lung homogenates after 3 day infection (as shown in FIG. 9) could be analyzed by ELISA. Values represent the mean±SEM. \*\*$P<0.005$, \*\*\*$P<0.0005$, statistically using unpaired t-tests.

Reference was made to FIG. 9, which showed a scatter graph of IFN-α amount (pg/mL) in the lung of mice after 3 days administration with the mutant virus (IAV/PR8) or the wild-type virus (IAV/PR8) according to an embodiment of the present invention. As shown in the result of FIG. 9, the mice infected intranasally (i.n.) with NS1 mutant virus could increase the IFN-α amount in the lung during a short period (3 days) (more than 2000 μg/mL), leading to better immune response and better immunoprotection.

Figure 10:
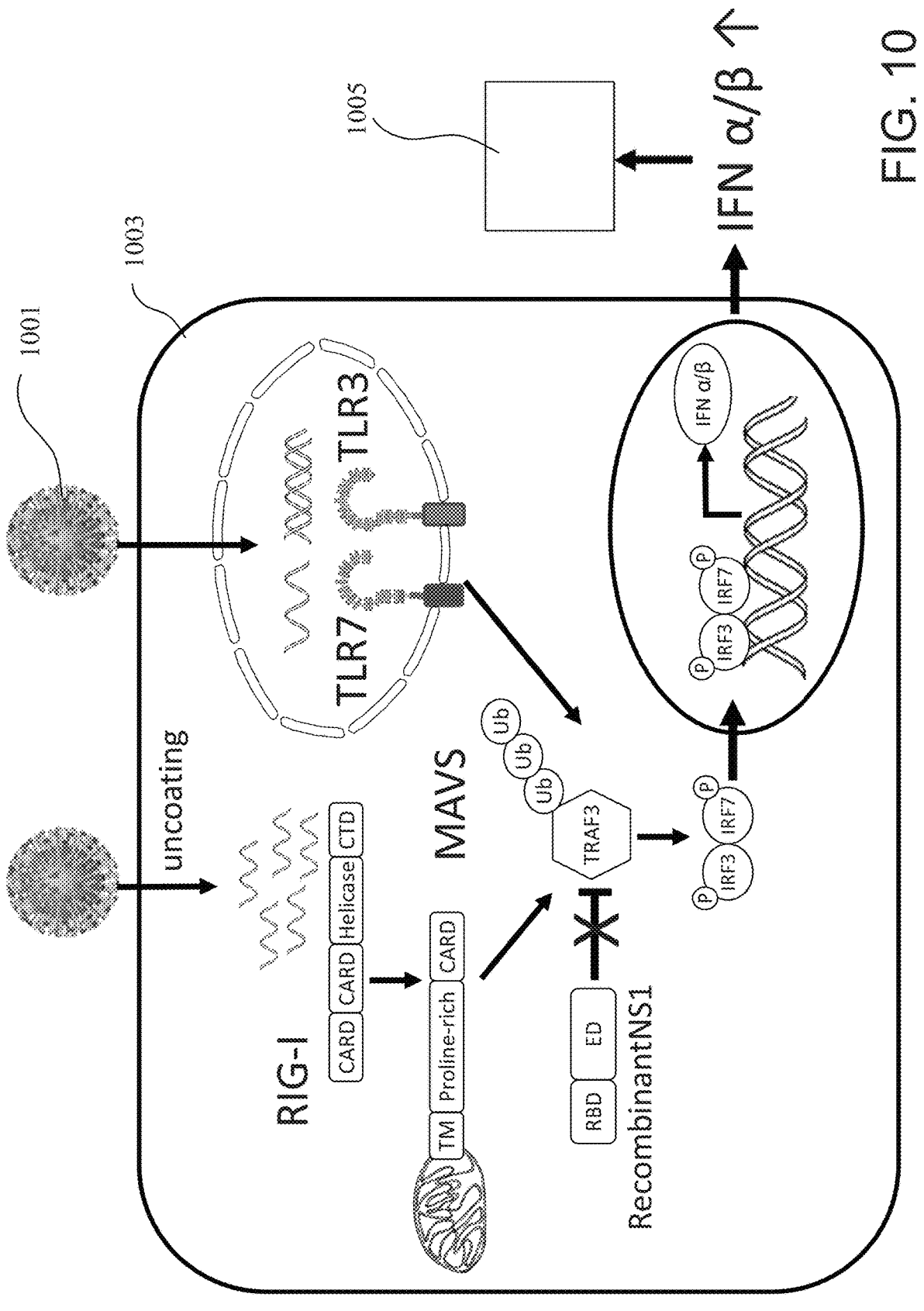
FIG. 10 shows a schematic diagram of possible mechanism of NS1 mutant according to an embodiment of the present invention.

In summary, the aforementioned embodiments demonstrate that the recombinant influenza virus containing the recombinant NS1 protein of the present invention remain NS1 and site mutation is introduced into NS1, resulting in the recombinant influenza virus with comparable replication ability to the wild-type virus. Such recombinant influenza virus can achieve efficacy of suppressing influenza virus via reducing the level of suppressing TRAF3, as well as increasing TLR3, TLR7 and RIG-I pathways to activate the type I interferon. Reference was made to FIG. 10, which showed a schematic diagram of possible mechanism of NS1 mutant according to an embodiment of the present invention. As shown in FIG. 10, after the influenza virus 1001 is uncoated and enter the cell 1003, the influenza virus 1001 suppresses the type I interferon for mediating immune evasion. However, the NS1 mutant (i.e. the recombinant NS1) can bind to TRAF3, block the activation of TRAF3, simultaneously affect RIG-I, TLR3 and TLR7 pathways, so as to elevate the expression level of the type I interferon and to cause the effect shown as the box 1005. More specifically, the box 1005 at least represents many effects as follows. Firstly, NS1 mutant can promote the activation of type I interferon in the lung of mice, for inducing better anti-viral protection ability. Moreover, the NS1 mutant preserve the most structure of the viral NS1 protein, except for site mutation or deletion, the recombinant influenza virus including the NS1 mutant can maintain the comparable replication ability to the wild-type virus, for being beneficial in subsequent production. Furthermore, the aforementioned in vivo experiment has demonstrated that the recombinant influenza virus including the recombinant NS1 can induce better immune response, reduce the death due to the influenza virus, and provide better immunoprotection against secondary viral infection, low toxicity and higher safety, thereby being applied for the method of treating or preventing a disease or condition caused by or associated with an influenza virus in a subject in need thereof.

It should be supplemented that, specific amino acid sequences, specific virus type, specific evaluating methods or specific subject are exemplified for clarifying the recombinant nonstructural protein 1, the recombinant influenza virus and the immunological composition including the same. However, as is understood by a person skilled in the art, other amino acid sequences, other virus type, other evaluating methods or other subject can be also adopted in the recombinant nonstructural protein 1, a recombinant influenza virus and an immunological composition including the same without departing the spirit and scope of the present invention rather than being limited as aforementioned.

It should be further supplemented that, the aforementioned experiments demonstrate that, there is one mutation or deletion introduced into at least one amino acid residue of the four continuous amino acid residues of TIMs of the recombinant NS1 of the present invention, and the resultant recombinant virus can achieve similar effects as aforementioned. For example, the amino acid sequences listed as SEQ ID NOs: 2, 21, 29, 37, 43 and 49 have the common structural features, and the results of the resultant recombinant virus (encoding to the amino acid sequence listed as SEQ ID NO:2) can correspond to the results of the recombinant virus (encoding to the amino acid sequence listed as SEQ ID NOs: 21, 29, 37, 43 and 49).

According to the embodiments of the present invention, the recombinant nonstructural protein 1, the recombinant influenza virus and the immunological composition including the same of the present invention have advantages that the recombinant influenza virus including the NS1 mutant can maintain the comparable replication ability to the wild-type virus, for elevating the interferon activating ability of the subject, inducing better immune response and providing better immunoprotection, thereby being applied for the method of treating or preventing a disease or condition caused by or associated with an influenza virus in a subject in need thereof.

Although the present invention has been described in considerable detail with reference to certain embodiments thereof, other embodiments are possible. Therefore, the spirit and scope of the appended claims should not be limited to the description of the embodiments contained herein.

---

What is claimed is:

1. A recombinant nonstructural (NS) protein 1, wherein amino acid residues of the recombinant NS 1 corresponding to the $2^{nd}$ to the $4^{th}$ amino acid residues of TRAF3-interacting motifs (TIMs) of wild-type NS 1 are selected from the group consisting of the $1^{st}$ to the $3^{rd}$ amino acid residues of amino acid sequences listed as SEQ ID NOs: 55 and 60, and the $2^{nd}$ to the $4^{th}$ amino acid residues of the TIMs of the wild-type NS 1 comprises the $2^{nd}$ to the $4^{th}$ amino acid residues of an amino acid sequence listed as SEQ ID NO: 1.

2. A recombinant NS protein 1, characterized that an amino acid sequence of the recombinant NS protein 1 corresponding to the $1^{st}$ to the $4^{th}$ amino acid residues of TIMs of wild-type NS 1 is encoded by a nucleic acid sequence selected from the group consisting of any one listed as SEQ ID NOs: 8 and 9, and the $1^{st}$ to the $4^{th}$ amino acid residues of the TIMs of the wild-type NS 1 comprises the Ind to the $4^{th}$ amino acid residues of an amino acid sequence listed as SEQ ID NO: 1.

3. A recombinant influenza virus comprising hemagglutinin (HA), neuraminidase (NA), nucleoprotein (NP), matrix (M) protein, polymerase basic protein 1 (PB1), PB2, polymerase acidic protein 1 (PA), which is characterized that the recombinant influenza virus further comprises the recombinant NS protein 1 of claim 1, and at least one amino acid residue of the NP, the M protein, the PB1, the PB2 and the PA protein has site mutation.

4. A recombinant influenza virus comprising hemagglutinin (HA), neuraminidase (NA), nucleoprotein (NP), matrix (M) protein, polymerase basic protein 1 (PB1), PB2, polymerase acidic protein 1 (PA) and a recombinant NS protein 1, which is characterized that the recombinant NS protein 1 comprises an amino acid sequence listed as any one of SEQ ID NOs: 55 and 60, at least one amino acid residue of the PB2 and the M protein has at least one site mutation, and the at least one amino acid residue of the NS protein 1 has site mutation except for the amino acid sequence.

5. The recombinant influenza virus of claim 4, wherein the recombinant influenza virus is originated from influenza A virus.

6. The recombinant influenza virus of claim 3, wherein the recombinant influenza virus is originated from H1N1 subtype, H2N2 subtype, H3N2 subtype, H5N1 subtype and/or H7N9 subtype.

7. The recombinant influenza virus of claim 4, wherein the recombinant influenza virus is originated from H1N1 subtype, H2N2 subtype, H3N2 subtype, H5N1 subtype and/or H7N9 subtype.

8. An immunological composition, comprising a recombinant influenza virus of claim 3 and a medically available carrier.

9. An immunological composition, comprising a recombinant influenza virus of claim 4 and a medically available carrier.

* * * * *